(12) United States Patent
Schraa et al.

(10) Patent No.: US 10,399,876 B2
(45) Date of Patent: Sep. 3, 2019

(54) AMMONIA-BASED AERATION CONTROL WITH SRT CONTROL

(71) Applicant: inCTRL Solutions Inc., Oakville (CA)

(72) Inventors: Oliver Schraa, Dundas (CA); Leiv Rieger, Oakville (CA)

(73) Assignee: inCTRL Solutions Inc., Oakville (CA)

( * ) Notice: Subject to any disclaimer, the term of this patent is extended or adjusted under 35 U.S.C. 154(b) by 202 days.

(21) Appl. No.: 15/712,601

(22) Filed: Sep. 22, 2017

(65) Prior Publication Data

US 2018/0354828 A1 Dec. 13, 2018

Related U.S. Application Data

(60) Provisional application No. 62/517,511, filed on Jun. 9, 2017.

(51) Int. Cl.
| | | |
|---|---|---|
| *C02F 3/12* | (2006.01) | |
| *G05B 19/05* | (2006.01) | |
| *G05B 17/02* | (2006.01) | |
| *G05B 15/02* | (2006.01) | |
| *G05D 21/00* | (2006.01) | |
| *G05D 7/00* | (2006.01) | |

(Continued)

(52) U.S. Cl.
CPC ............... *C02F 3/12* (2013.01); *B01J 4/008* (2013.01); *C02F 1/74* (2013.01); *C02F 3/006* (2013.01); *G05B 11/42* (2013.01); *G05B 15/02* (2013.01); *G05B 17/02* (2013.01); *G05B 19/052* (2013.01); *G05D 7/00* (2013.01); *G05D 16/20* (2013.01); *G05D 21/00* (2013.01); *A61L 2/24* (2013.01); *C01B 21/087* (2013.01); *C02F 3/1263* (2013.01); *C02F 3/302* (2013.01); *C02F 2209/005* (2013.01); *C02F 2209/10* (2013.01); *C02F 2209/14* (2013.01); *C02F 2209/22* (2013.01); *G05B 9/03* (2013.01)

(58) Field of Classification Search
None
See application file for complete search history.

(56) References Cited

U.S. PATENT DOCUMENTS

| | | | |
|---|---|---|---|
| 2008/0314841 A1* | 12/2008 | Moon | C02F 3/006 210/746 |
| 2014/0069863 A1* | 3/2014 | Wett | C02F 3/006 210/605 |
| 2014/0263041 A1* | 9/2014 | Regmi | C02F 3/006 210/605 |

OTHER PUBLICATIONS

Schraa et al., Coupling SRT Control with Aeration Control Strategies, Proceedings of WEFTEC 2016, 2016, pp. 4824-4839.
(Continued)

*Primary Examiner* — Matthew D Krcha
(74) *Attorney, Agent, or Firm* — Hodgson Russ LLP

(57) ABSTRACT

Total ammonia nitrogen in a volume of sludge in an aeration tank is measured and compared to a target ammonia nitrogen setpoint to calculate an airflow target for adjusting the measured total ammonia nitrogen toward the target ammonia nitrogen setpoint. The airflow target may be an airflow rate or, for an SBR, an airflow duration, and airflow into the aeration tank is adjusted according to the airflow target. A target solids retention time setpoint is also calculated from information relating to the airflow target and the solids retention time is adjusted toward the target solids retention time setpoint. The waste activated sludge flow rate for the aeration tank may be adjusted to adjust the solids retention time for the aeration tank toward the target solids retention time setpoint.

18 Claims, 18 Drawing Sheets

(51) Int. Cl.
*B01J 4/00* (2006.01)
*C02F 1/74* (2006.01)
*G05B 11/42* (2006.01)
*G05D 16/20* (2006.01)
*C02F 3/00* (2006.01)
*G05B 9/03* (2006.01)
*A61L 2/24* (2006.01)
*C01B 21/087* (2006.01)
*C02F 3/30* (2006.01)

(56) References Cited

OTHER PUBLICATIONS

Amand et al., Aeration control—a review, Wat. Sci. & Tech, vol. 67, No. 11, 2374-2398, 2013.
Brewer et al., Plant Optimization Using Online Phosphorus Analyzers and Automated SRT Control to Achieve Harbour Delisting, Proceedings of WEFTEC 1995, 1995.
Ciancone et al., Tune Controllers to Meet Your Performance Goals, Control, vol. 5, pp. 50-57, 1992.
Dold, Quantifying Sludge Production in Municipal Treatment Plants, Proceedings of WEFTEC 2007, 2007.
Ekama et al., Biological Wastewater Treatment: Principles, Modelling and Design, Chapters 4 and 5, 2008.
Garrett, Hydraulic Control of Activated Sludge Growth Rate, Sew. Ind. Wastes, vol. 39, No. 3, 1958.
Ekster et al., Automatic Waste Control, Proceedings of the 1st IWA International Conference on Instrumentation, control and Automation, 2001.
Langergraber et al., Generation of diurnal variation for influent data for dynamic simulation, Wat. Sci. & Tech., vol. 57, No. 9, 2008.
Langergraber et al., Using numerical simulation to optimize control strategies during activated sludge plant design, Proceedings of the 10th IWA Conference on Instrumentation, Control and Automation (ICA), 2009.
Otterpohl et al., Dynamic models for clarifers of activated sludge plants with dry and wet weather flows, Wat. Sci. & Tech., vol. 26, Nos. 5-6, pp. 1391-1400, 1992.
Rieger et al., Improving nutrient removal while reducing energy use at three Swiss WWTPs using advance control, Water Environ. Res., vol. 84, No. 2, pp. 171-189, 2012.
Rieger et al., Ammonia-based feedforward and feedback aeration control in activated sludge processes, Water Environ. Res., vol. 86, No. 1, pp. 63-73, 2014.
Schraa et al., Coupling SRT control with aeration control strategies, Proceedings of WEFTEC 2016, 2016.
Schraa et al., Development of a model for activated sludge aeration systems: linking air supply, distribution, and demand, Wat. Sci. & Tech., Oct. 2016.
Stephenson et al., Automatic Control of Solids Retantion Time and Dissolved Oxygen in the Activated Sludge Process, Wat. Sci. & Tech., vol. 13, pp. 751-758, 1981.
Takacs, Experiments in Activated Sludge Modelling, PhD Thesis, Ghent University, Belgium, pp. 267, 2008.
Takacs et al., A dynamic model of the thickening/clarification process, Wat. Res., vol. 25, No. 10, pp. 1261-1271, 1991.
Takacs et al., The dynamic solids residence time, Proceedings of IWA World Water Congress 2002, 2002.
U.S. Environmental Protection Agency, Office of Research and Development, Design Manual: Fine Pore Aeration Systems, EPA/625/1-89/023, 1989.
Vaccari et al., Feedback control of activated sludge waste rate, Journal WPCF, vol. 60, 1979-1985, 1988.
Vaccari et al., Calculation of mean cell residence time for unsteady-state activated sludge systems, Biotech. and Bioeng., vol. 27, pp. 695-703, 1985.
Van Haandel et al., Handbook of Biological Wastewater Treatment: Design and Optimisation of Activated Sludge Systems, 2012.
WE, Automated Process Control Strategies, Water Environment Federation, 1997.

* cited by examiner

US 10,399,876 B2

AMMONIA-BASED AERATION CONTROL WITH SRT CONTROL

CROSS-REFERENCE TO RELATED APPLICATION

This application claims priority to U.S. Provisional Application No. 62/517,511 filed on Jun. 9, 2017, the teachings of which are hereby incorporated by reference.

TECHNICAL FIELD

The present disclosure relates to water resource recovery facilities, also known as wastewater treatment plants, and more particularly to ammonia-based aeration control for controlling total ammonia nitrogen in an activated sludge process.

BACKGROUND

Although certain previously published documents are referred to in the specification, this is to assist the reader in understanding the specification; and none of these documents is admitted to be prior art against the present application. In particular, and without limitation, one or more of the documents referred to may be disclosures made by the inventor or joint inventor or by another who obtained the subject matter disclosed directly or indirectly from the inventor or a joint inventor and were published less than one year before the effective filing date.

Reference is now made to FIG. 1, which is a simplified schematic flow diagram for an exemplary water resource recovery facility, indicated generally by reference 100, which uses an activated sludge process. In such water resource recovery facilities, wastewater 102 is collected in lateral sewers serving both residential and industrial urban areas and these lateral sewers connect with larger trunk sewers that convey the wastewater 102 to the water resource recovery facility (also known as a wastewater treatment plant). As the wastewater 102 enters the water resource recovery facility it flows through bar racks and screens 110 to remove floating objects that can clog pumps and pipes, the objects that are removed are referred to as "screenings" 112. After the wastewater 102 has been screened it passes into a grit chamber 114 where sand, grit, and small stones 116 are removed from the wastewater 102. Screening and grit removal are known as preliminary treatment steps. With the screening and grit removal completed, the wastewater 102 still contains dissolved organic and inorganic matter and suspended solids. A portion of the suspended solids are removed using primary clarifiers 118 downstream of the grit chambers 114. In the primary clarifiers 118, the suspended solids have time to settle and are removed as raw sludge (also known as primary sludge) 120.

After preliminary and primary treatment, the wastewater 102 flows into aeration tanks 122 where the wastewater 102 is mixed with air and a concentrated stream of bacteria. The air is introduced using blowers that force air through pipes that feed diffusers within the aeration tanks. The wastewater 102 remains in the aeration tanks for several hours and the bacteria consume the organic matter contained in the wastewater. The organic matter is used for the synthesis of new bacterial cells and the production of the energy required for cell metabolism. A certain type of bacteria can also convert ammonia into nitrite and nitrate to provide its energy requirements in a process known as nitrification.

From the aeration tanks 122, the wastewater, which is now referred to as "mixed liquor" and denoted by reference 104, flows into secondary clarifiers 124 which remove the bacteria and other solids so that the treated effluent, denoted by reference 106, is suitable for downstream disinfection in a disinfection unit 126, such as a chlorination unit or a UV disinfection unit. The disinfected effluent 108 can then be discharged. In some cases, effluent may be discharged without disinfection.

The secondary clarifiers 124 also serve to thicken or concentrate the bacteria within the mixed liquor 104. This thickened stream of bacteria is known as the return activated sludge (RAS), denoted by reference 106A, and is recycled and mixed with the wastewater 102 leaving the primary clarifiers. Because the bacteria are continuously reproducing and the RAS stream 106A is recycling the bacteria, the mass of sludge will continue to increase without limit unless excess sludge, denoted by reference 166B, is wasted from the system 100. Excess sludge 166B is wasted or purged from the system by splitting off a portion of the return activated sludge 106A and sending it for thickening and stabilization and further volume reduction in aerobic or anaerobic digesters. The excess sludge 166B is known as waste activated sludge (WAS) 166B, and can alternatively be taken directly from the aeration tanks. In order to eliminate the need for thickener to concentrate the WAS, it can also be sent to the primary clarifiers.

The above description of an exemplary water resource recovery facility is provided to facilitate understanding of the context in which aspects of the presently disclosed technology may be applied, and is not intended to be limiting. One skilled in the art will appreciate that the water resource recovery facility described above is merely one exemplary implementation of such a facility, and that many variations and alternate arrangements are possible and that the presently disclosed technology may be applied to activated sludge processes in a wide variety of water resource recovery facilities.

Ammonia-based aeration control, also referred to by the acronym ABAC (Rieger et al., 2014), is a cascade control concept for controlling total ammonia nitrogen ($NH_x$—N), which is the sum of $NH_3$—N plus $NH_4$—N in an activated sludge process. Its main goals are to tailor the aeration intensity to the $NH_x$—N loading and to maintain consistent nitrification, which meets effluent limits but limits energy consumption and improves nutrient removal (Rieger et al., 2012).

One limitation to ABAC is that the solids retention time (SRT) control strategy used at a water resource recovery facility (WRRF) may not be consistent with the goals of ABAC. For example, ABAC may not be able to handle peak loads if the SRT is too low and may reach minimum airflow constraints if the solids retention time (SRT) is too high.

SUMMARY

In order to overcome the above limitation, an ABAC system is combined with a dynamic SRT controller; this is referred to herein as "ABAC-SRT" control. According to the ABAC-SRT control approach, a higher-level supervisory controller is used to coordinate the two controllers. The supervisory controller determines an SRT setpoint that supports ammonia-based aeration control.

In one aspect, a method of supervisory control for an activated sludge-based water resource recovery facility is described. The method is applied to at least one aeration tank, and comprises measuring total ammonia nitrogen in a volume of sludge in the aeration tank(s) and comparing the measured total ammonia nitrogen to a target ammonia nitrogen setpoint to calculate a target dissolved oxygen setpoint for adjusting the measured total ammonia nitrogen toward the target ammonia nitrogen setpoint. The method further comprises measuring dissolved oxygen in the volume of sludge in the aeration tank(s) and comparing the measured dissolved oxygen to the target dissolved oxygen setpoint to calculate a target airflow setpoint for adjusting the measured dissolved oxygen toward the target average dissolved oxygen setpoint, and adjusting airflow into the aeration tank toward the target airflow setpoint. The method still further comprises comparing the target dissolved oxygen setpoint to a desired dissolved oxygen concentration to calculate a target solids retention time setpoint, and adjusting a solids retention time for the aeration tank(s) toward the target solids retention time setpoint.

The solids retention time for the aeration tank(s) may be adjusted toward the target solids retention time setpoint by adjusting the waste activated sludge flow rate.

In some embodiments, adjusting the waste activated sludge flow rate comprises comparing the target solids retention time setpoint to a calculated dynamic solids retention time to calculate a target mixed liquor suspended solids setpoint, measuring a mixed liquor suspended solids concentration in the aeration tank(s), comparing the measured mixed liquor suspended solids concentration to the target mixed liquor suspended solids setpoint to calculate a target waste activated sludge flow rate setpoint and adjusting the waste activated sludge flow rate toward the target waste activated sludge flow rate setpoint.

In some embodiments, adjusting airflow into the aeration tank toward the target airflow setpoint is carried out by a dissolved oxygen controller adjusting airflow directly by controlling at least one valve. In other embodiments, adjusting airflow into the aeration tank toward the target airflow setpoint comprises a dissolved oxygen controller adjusting airflow by sending the target airflow setpoint to an airflow controller that controls the valve, with the airflow controller receiving feedback from a measured airflow.

The method may further comprise applying a low-pass filter to the calculated dynamic solids retention time or to measured or estimated quantities used in its calculation.

In some embodiments, the target average dissolved oxygen setpoint is calculated by an ammonia controller, the target airflow setpoint is calculated by a dissolved oxygen controller and the target solids retention time setpoint is calculated by a supervisory controller. In certain particular embodiments, the target mixed liquor suspended solids setpoint is calculated by a solids retention time controller and the target waste activated sludge flow rate setpoint is calculated by a mixed liquor suspended solids controller. The ammonia controller, the dissolved oxygen controller, the supervisory controller, the solids retention time controller and the mixed liquor suspended solids controller may each be a distinct individual programmable logic controller, or a software module executing in at least one processor of a computer.

In some embodiments, the method may be applied to an activated sludge-based water resource recovery facility comprising a plurality of aeration tanks, and in such embodiments adjusting the solids retention time for the at least one aeration tank toward the target solids retention time setpoint may comprise temporarily ceasing inflow to at least one of the plurality of aeration tanks.

In some embodiments, the airflow is intermittent and adjusting airflow into the aeration tank(s) toward the target airflow setpoint may comprise adjusting aeration period length.

In some embodiments, the method may further comprise adding nitrifying sludge to the aeration tank(s) and adjusting the solids retention time for the aeration tank(s) toward the target solids retention time setpoint accounts for addition of the nitrifying sludge.

In certain embodiments, support media are disposed within the aeration tank(s), with the support media being adapted to allow biofilm growth on the support media.

In another aspect, a method of supervisory control for an activated sludge-based water resource recovery facility may be applied to at least one sequencing batch reactor (SBR) in the water resource recovery facility. The method comprises measuring total ammonia nitrogen in a volume of sludge in the SBR(s) during an aerobic phase of the SBR(s), comparing the measured total ammonia nitrogen to a target ammonia nitrogen setpoint to calculate a target aerobic phase length, and adjusting a duration of airflow into the SBR(s) toward the target aerobic phase length.

The method may further comprise using the target aerobic phase length to adjust a target solids retention time setpoint, and adjusting the waste activated sludge flow rate for the SBR(s) during the aerobic phase according to the solids retention time setpoint.

The methods may be applied in the contexts of conventional activated sludge-based water resource recovery facilities as well as in the context of granular sludge reactors.

BRIEF DESCRIPTION OF THE DRAWINGS

These and other features will become more apparent from the following description in which reference is made to the appended drawings wherein.

DETAILED DESCRIPTION

Figure 1:
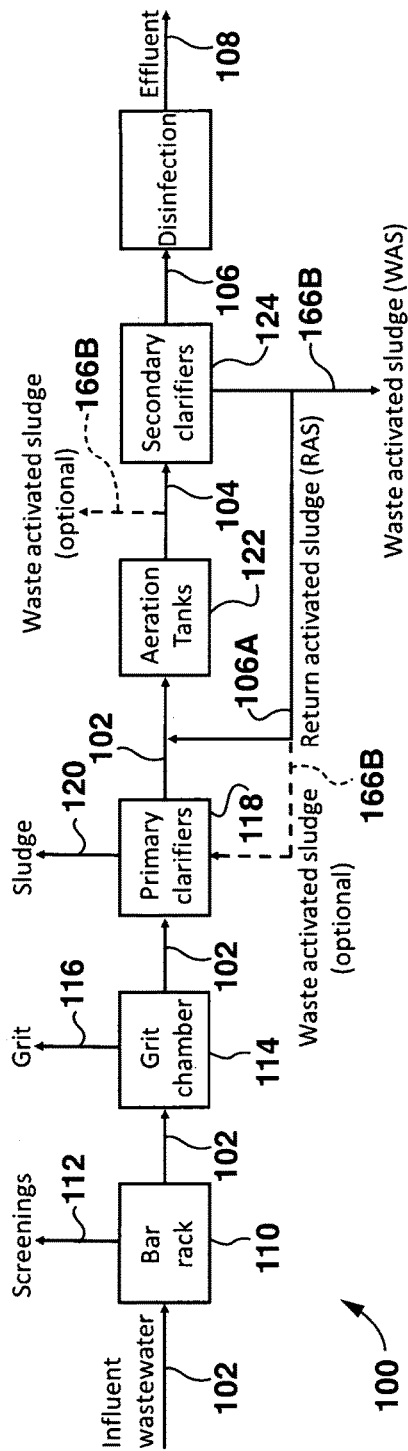
FIG. 1 is a simplified schematic flow diagram for an exemplary water resource recovery facility.

ABAC-SRT control is a strategy for aligning the goals of ammonia-based aeration control (ABAC) and solids retention time (SRT) control. A supervisory controller may be used to adjust the SRT setpoint to support ammonia-based aeration control.

The SRT, also known as the sludge age or mean cell residence time, is an important design and control parameter for the activated sludge process. It expresses the average length of time that bacteria stay in the process before being wasted or lost in the effluent. Maintaining an appropriate SRT is necessary to ensure a well-flocculated sludge that settles quickly and supports full-nitrification throughout the year and especially at winter temperatures.

In the wastewater treatment literature, SRT is usually considered from a steady-state perspective. At steady-state, the static SRT is defined as the mass of microorganisms in the system divided by the mass of microorganisms wasted per day:

$$SRT = \frac{X_{MLSS} V_a}{X_{RAS} Q_w + X_e Q_e} \quad (1)$$

where:
$V_a$=total volume of aeration tanks, m³
$X_{MLSS}$=total or volatile suspended solids concentration in the mixed liquor, mg/L
$X_{RAS}$=total or volatile suspended solids concentration in the return activated sludge (RAS), mg/L
$X_e$=total or volatile suspended solids concentration in the secondary effluent, mg/L
$Q_w$=waste activated sludge flow rate, m³/d
$Q_e$=secondary effluent flow rate, m³/d As shown in Equation 1, the volatile suspended solids (VSS) or total suspended solids (TSS) concentrations are typically used as surrogate measurements for the microorganism concentrations. The static SRT is only equal to the actual SRT at steady-state because if the waste activated sludge (WAS) flow rate is changed the formula suggests that the SRT has instantly changed, which is not true in reality because the system takes considerable time to respond. Equation 1 ignores the active microorganisms in the clarifier sludge blanket which could be significant but are difficult to measure accurately.

For a completely-mixed activated sludge system, a mass balance on microorganisms can be re-arranged to calculate the specific substrate utilization rate, which is the mass of substrate utilized per day per mass of active microorganisms:

$$U = \frac{1 + b_h SRT}{Y(SRT)} \quad (2)$$

where:
U=specific substrate utilization rate, mass COD/mass VSS/d
Y=activated sludge yield coefficient, mass VSS/mass COD
$b_h$=endogenous decay rate, $d^{-1}$ As shown in Equation 2, the specific substrate utilization rate is directly related to the yield, decay rate, and SRT. Both the activated sludge yield and decay rate are considered to be constant for practical purposes, leaving the SRT as the main parameter to control the utilization rate of substrate.

The SRT in a WRRF is typically controlled by adjusting the WAS flow rate. One especially important factor to consider in SRT control is the speed of response. A wastewater treatment plant's SRT takes at least two to three times the steady-state SRT to stabilize after a change in waste flow. As a result, SRT control cannot remove the variations in SRT caused by the diurnal loading variations. These occur at too high a frequency to be attenuated by changing the waste flow rate. The main goals of an SRT controller are to maintain a consistent SRT, and to respond to seasonal variations and storm events.

Equation 1 can be simplified by assuming that the biomass lost in the effluent is negligible. Using this assumption, a common SRT control strategy is hydraulic wasting (Garrett, 1958) where sludge is wasted directly from the aeration tanks and the desired waste flow rate becomes the volume of the aeration tanks divided by the desired SRT:

$$Q_w = \frac{V_a}{SRT} \quad (3)$$

When sludge is wasted from the recycle line, with recycle ratio r, the hydraulic wasting formula becomes (WEF, 1997):

$$Q_w = \left(\frac{r}{r+1}\right) \frac{V_a}{SRT} \quad (4)$$

Stephenson et al. (1981) and Brewer et al. (1995) show practical applications of implementing hydraulic wasting strategies. Hydraulic wasting is simple to understand and execute, but one potential disadvantage is that for a constant SRT the waste flow does not vary and this may not be optimal during storm events and seasonal variations.

Figure 2:
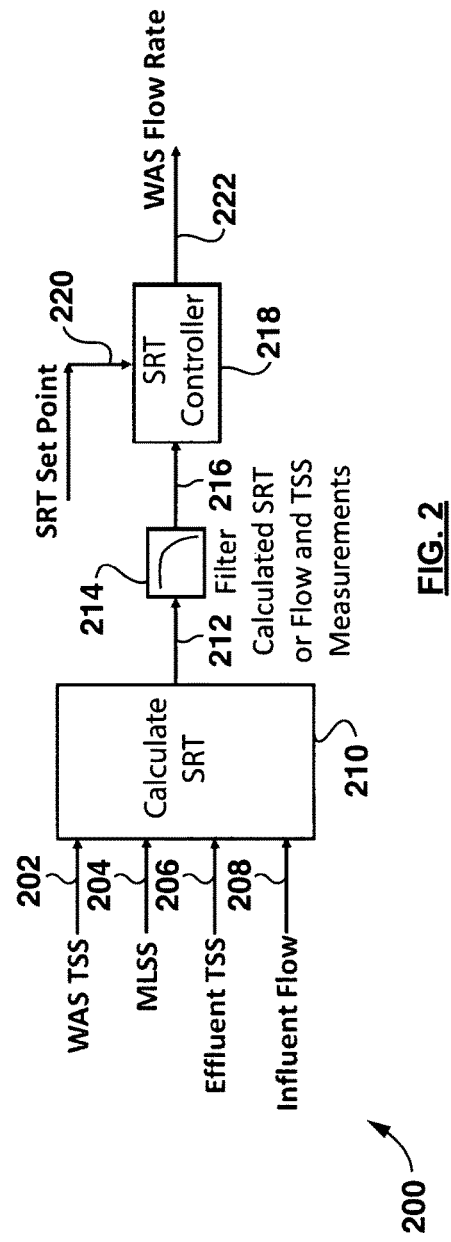
FIG. 2 is a schematic diagram showing an exemplary control concept for automatic SRT control.

SRT can also be controlled with an automatic feedback control algorithm that uses on-line measurements of mixed liquor suspended solids (MLSS), recycled activated sludge total suspended solids (RAS TSS) and waste flow rate as suggested by Vaccari et al. (1988) and Ekster (2001). A potential algorithm could use the on-line measurements to calculate the SRT using Equation 1, filter the static SRT using a low-pass filter, and have the feedback controller adjust the waste flow rate to keep the filtered SRT at the setpoint. The concept is illustrated in FIG. 2, in which an exemplary control concept for automatic SRT control is indicated generally by reference 200. The waste activated sludge total suspended solids (WAS TSS) measurements 202, mixed liquor suspended solids (MLSS) measurements 204, effluent total suspended solids (TSS) measurement 206 and influent flow measurement 208 are fed to a calculation engine 210. The calculation engine 210 may be implemented, for example, in a programmable logic controller or a suitably programmed general purpose computer. The calculation engine 210 calculates a static SRT 212, which is fed to a low pass filter 214. The filtered SRT 216 is fed to an SRT controller 218, which also receives an SRT setpoint 220 and uses the filtered SRT 216 and the SRT setpoint 220 to determine a waste activated sludge flow rate 222 for the system. As shown in FIG. 2, filtering of the SRT calculation (or of the influent flow and TSS measurements 202, 204, 206, 208 used to calculate the static SRT 212) is used because the steady-state SRT responds too rapidly to dynamic process variations and setpoint changes. Using a moving average SRT is not ideal as its response is not smooth enough for proper feedback control.

Vaccari et al. (1985) developed a dynamic sludge age (DSA) function based on an age balance equation in order to overcome the limitations of the static SRT. Analytical expressions for the DSA were developed by Vaccari et al. (1985) for four common cases. Takács and Patry (2002) and Takács (2008), developed the dynamic SRT (DSRT) which is the solution of the following ordinary differential equation:

$$dSRT/dt = 1 - SRT(F\_p)/M \quad (5)$$

where:
$dSRT/dt$=age change of solids (change in age of solids [in days] per days of real time)
M=mass of solids in the system
F_p=mass flow of solids produced in the system (true sludge production)

The DSA of Vaccari et al. (1985) and the DSRT of Takács and Patry (2002) can be shown to be equivalent using simulation provided that the same definitions are used for model variables such as the true sludge production. Takács (2008) estimated the true sludge production using a model presented by Dold (2007). Alternatively, the true sludge production can be estimated using the following equation from Vaccari et al. (1988):

$$F\_p = (M - M\_o)/\Delta t + Q\_w X\_w + Q\_e X\_e \quad (6)$$

where:
M=mass of total or volatile solids in the system at the current time (g);
M_o=mass of total or volatile solids in the system at the previous time interval (g);
$\Delta t$=time interval between calculations of the sludge production (d);
Q_w=waste flow rate (m³/d);
X_w=total or volatile solids concentration of waste stream (g/m³);
Q_e=secondary effluent flow rate (m³/d); and
X_e=total or volatile solids concentration of secondary effluent stream (g/m³).

Vaccari et al. (1988) proposed feedback proportional-integral-derivative (PID) control of the DSA, but their investigations did not consider how the SRT setpoint itself should be determined.

Figure 3:
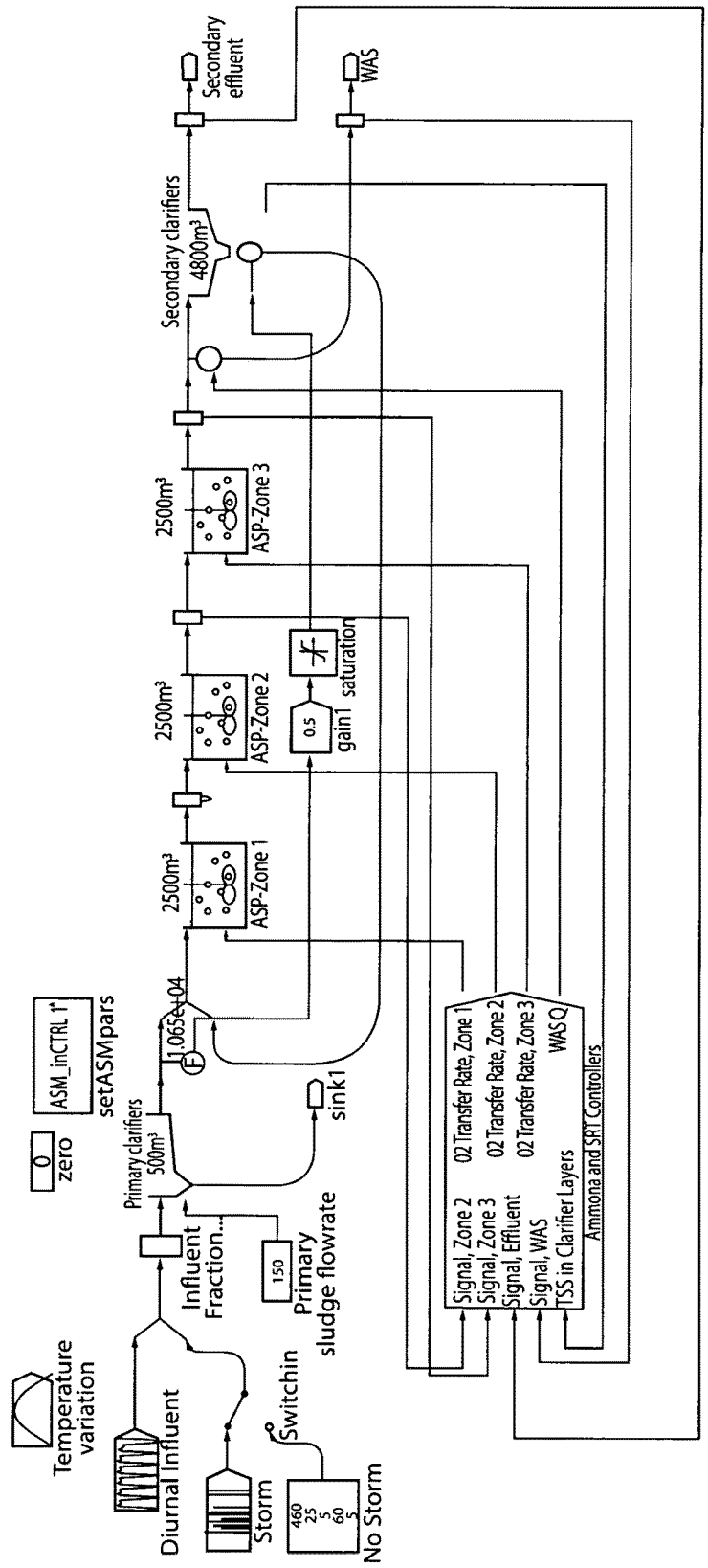
FIG. 3 shows an exemplary water resource recovery facility as represented using SIMBA#water simulation software.

A comparison of selected SRT calculation methods was performed using SIMBA#water, a dynamic simulator for sewers, WRRFs, and rivers. SIMBA#water is available from inCTRL Solutions Inc., having an address at 470 Anthony Drive, Oakville, Ontario, Canada L6J 2K5. The SRT calculations were compared using an example nitrifying WRRF presented by Ekama and Wentzel (2008). The model of the WRRF (FIG. 3) includes diurnal influent flow and chemical oxygen demand (COD), ammonia and ammonium nitrogen ($NH_x$), and soluble phosphorus (SP) concentration patterns, primary clarifiers, three bioreactors in series, and a layered clarifier model. A separate dissolved oxygen (DO) controller is used for each bioreactor and each DO controller sends an airflow setpoint to a lower level flow controller that manipulates a control valve. A detailed aeration system sub-model is included as part of the simulation model (Schraa et al., 2016b) to provide a realistic test environment. The aeration system model includes three 4,800 Nm³/h (3,075 scfm) turbo blowers, aeration piping including fittings (based on a typical aeration piping layout), and membrane disc diffusers. A total airflow controller adjusts the blower output and number of blowers in service to match the sum of the three airflow controller setpoints.

The diurnal patterns are created using the influent generation tool developed by the HSG group (Langergraber, 2008; Langergraber, 2009). The pattern is adjusted on the weekends so that the loadings are reduced by 10% and the patterns are delayed by 1 hour.

Proportional recycle is used, i.e. the RAS flow rate is proportional to the primary effluent flow rate, and wasting is done from the $3^{rd}$ bioreactor to provide an SRT of 11 days at design conditions. The SRT of 11 days was calculated as the minimum SRT for nitrification at 10° C., a desired steady-state effluent $NH_x$ concentration of 1 mgN/L, and a safety factor of 1.5 days using the design equation presented by van Haandel and van der Lubbe (2012).

The model of the example WRRF developed in SIMBA#water uses the inCTRL-ASM biokinetic model (with its default parameter values) along with the Otterpohl and Freund (1992) model for the primary clarifier and the Takács et al. (1991) clarification model for the secondary clarifiers.

The SRT calculation methods explored are as follows:
Dynamic SRT calculation (Equations 5 and 6)
Static SRT calculation (Equation 1)
Filtered Static SRT and a filter time constant of 7 days (Equation 1)
Hydraulic SRT (Equation 3 re-arranged to solve for SRT)

Dynamic simulations were conducted to compare the response of the SRT calculations to a step change in WAS flow rate and to a storm event at a wastewater temperature of 10° C.

Figure 4:
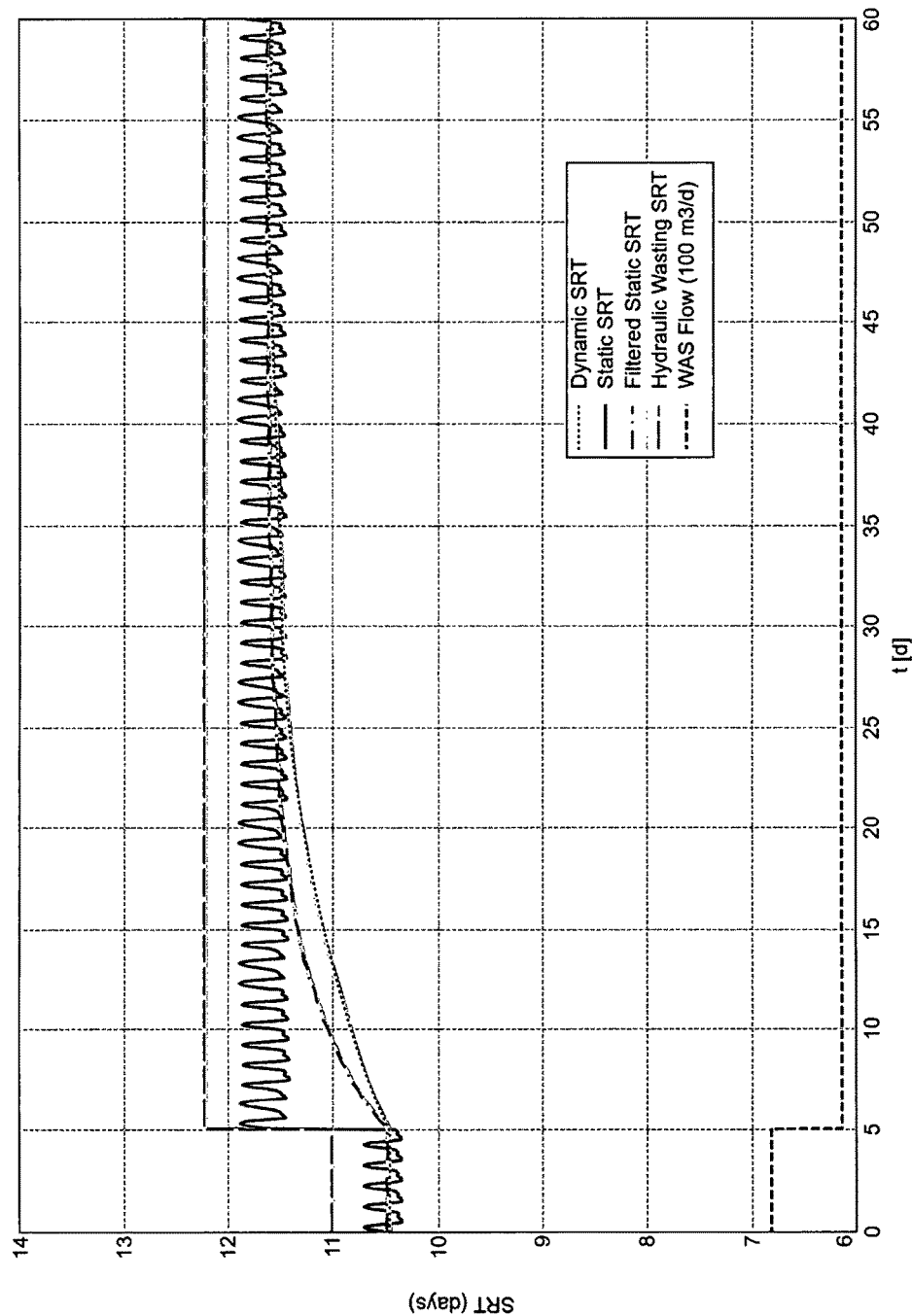
FIG. 4 is a graph showing a comparison of different SRT calculations after a step change in WAS flow rate.

A plot of the response of the different SRT calculation methods to a diurnal influent loading pattern with a step change in WAS flow rate at 5 days is shown in FIG. 4. The hydraulic SRT begins the simulation at 11 days while the other SRT values average 10.5 days as they consider the solids lost in the effluent. As shown in FIG. 4, the hydraulic SRT and the static SRT are very sensitive to changes in the WAS flow and instantly move to the new SRT. An instantaneous increase in SRT is unrealistic as the SRT cannot increase by more than one day per day with no wasting. The dynamic SRT responds much more smoothly and slowly to the change in WAS flowrate and is better suited to automatic SRT control. The filtered static SRT is a reasonable approximation to the dynamic SRT for changes in WAS flow, but the filter time constant used becomes a tuning parameter and would need to be varied depending on the desired SRT setpoint.

Figure 5:
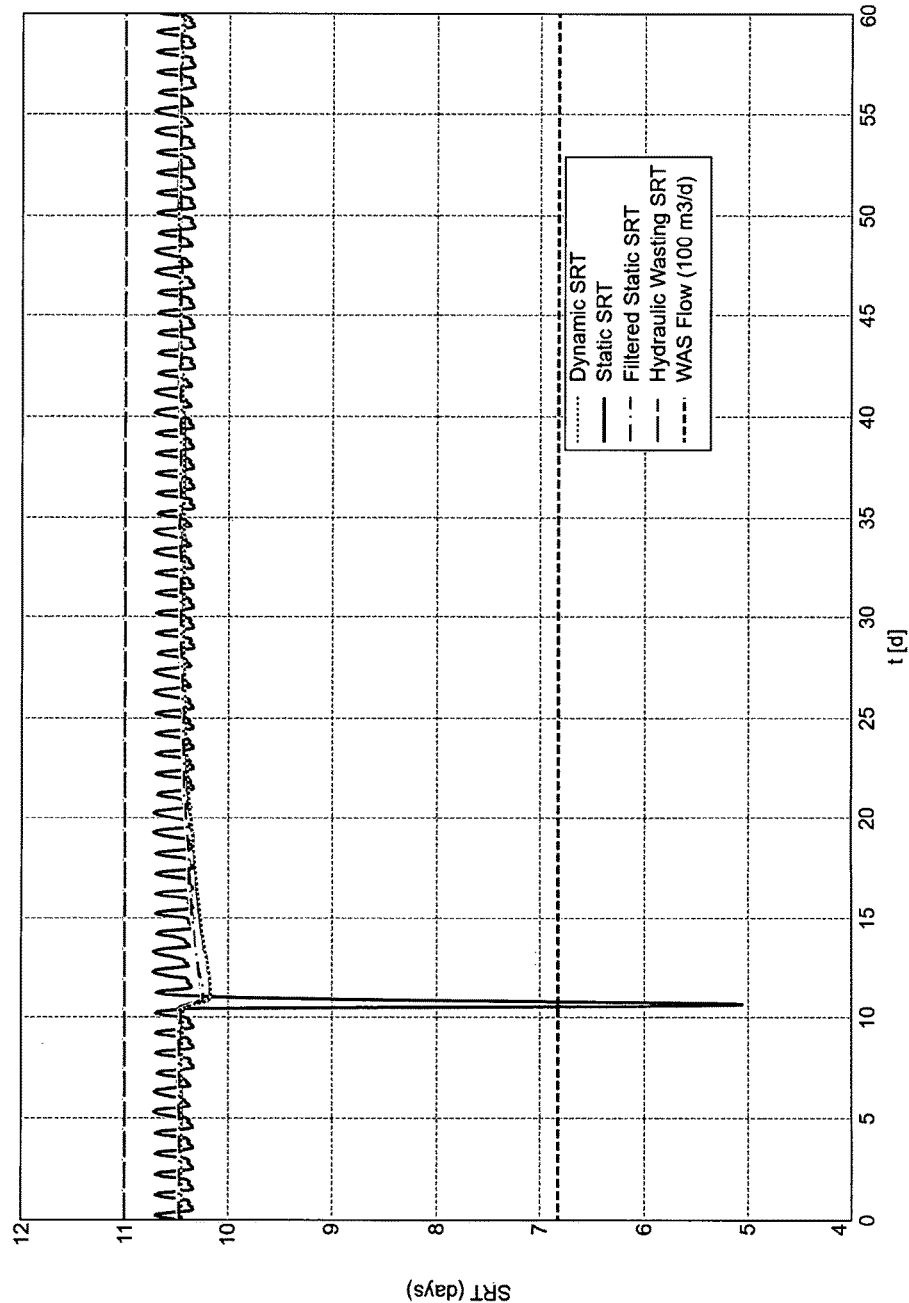
FIG. 5 is a graph showing a comparison of different SRT calculations after a storm event at a time of 10 days.

A plot of the response of the different SRT calculation methods to a diurnal influent loading pattern with a storm event that occurs after 10 days with a constant wasting rate is shown in FIG. 5. As shown, the hydraulic and traditional SRT calculation methods differ considerably from the dynamic SRT. The hydraulic SRT stays constant throughout the entire simulation because the wasting rate does not change. The static SRT calculation shows a large drop in the SRT during the storm, due to the loss of solids in the effluent, but then quickly returns back to its original value which is not possible because the SRT cannot increase by more than 1 day per day. Clearly, the hydraulic and static SRT calculations are unrealistic under storm conditions.

The dynamic SRT and the filtered static SRT both drop in response to the storm but do so more slowly and then take much longer to return to the original SRT. The dynamic SRT and the filtered static SRT are more realistic and appropriate for feedback control than the traditional or hydraulic wasting SRT calculations as they have a smoother dynamic response with the correct rate of change.

Figure 6:
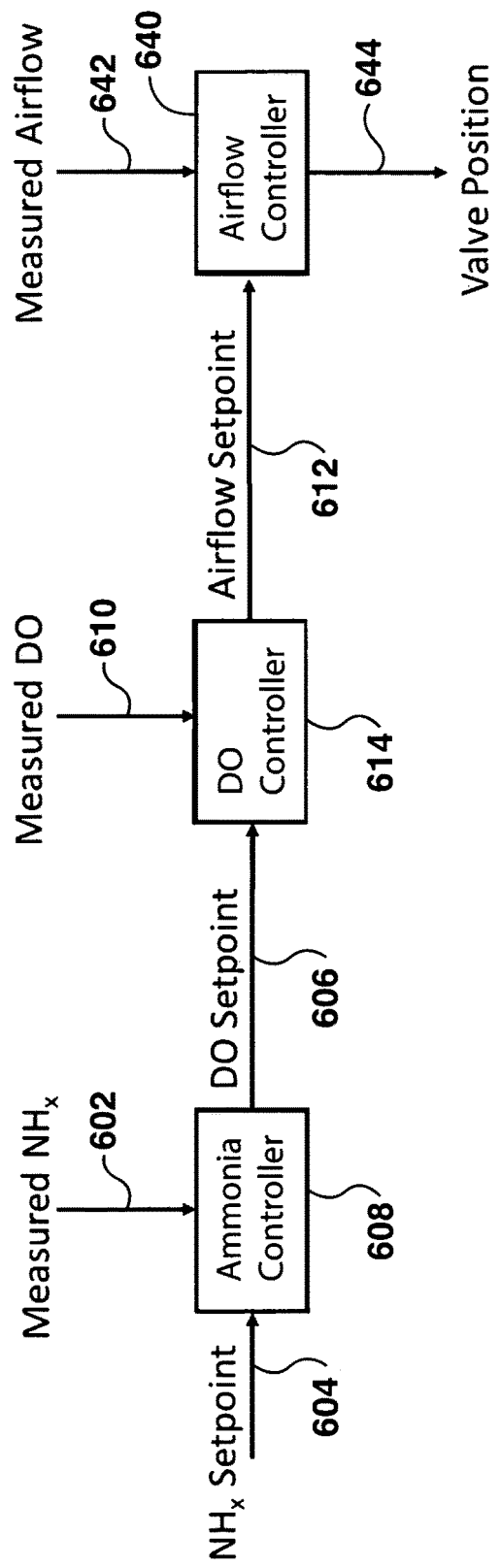
FIG. 6 is a schematic diagram showing an exemplary control concept for ammonia-based aeration control.

As discussed earlier, ammonia-based aeration control (ABAC) is a cascade control concept for controlling total ammonia nitrogen ($NH_x$—N) in the activated sludge process. A diagram illustrating the concept of ABAC is shown in FIG. 6, in which an exemplary control concept for ammonia-based aeration control is indicated generally at 600. According to the method 600, total ammonia nitrogen in a volume of sludge in an aeration tank (e.g. aeration tank 122) is measured and the measured total ammonia nitrogen 602 is compared to a target ammonia nitrogen setpoint 604 to calculate a target dissolved oxygen ("DO") setpoint 606 for adjusting the measured total ammonia nitrogen 602 toward the target ammonia nitrogen setpoint 604. In the illustrated embodiment, the target dissolved oxygen setpoint 606 is calculated by an ammonia controller 608. The ammonia controller 608 may be implemented, for example, by way of feedback loop, or a feed-forward controller, or a combination of both. A model-based ammonia controller may also be used. Dissolved oxygen in the volume of sludge in the aeration tank is measured, and the measured dissolved oxygen 610 is compared to the target dissolved oxygen setpoint 606 to calculate a target airflow setpoint 612 for adjusting the measured dissolved oxygen 610 toward the target dissolved oxygen setpoint 606. In the illustrated embodiment, the target airflow setpoint 612 is calculated by a dissolved oxygen controller 614. Airflow into the aeration tank is adjusted toward the target airflow setpoint 612 by the dissolved oxygen controller 614 sending the target airflow setpoint 612 to an airflow controller 640 that receives feedback from a measured airflow 642 and sends control signals 644 to a valve governing the airflow.

Figure 7:
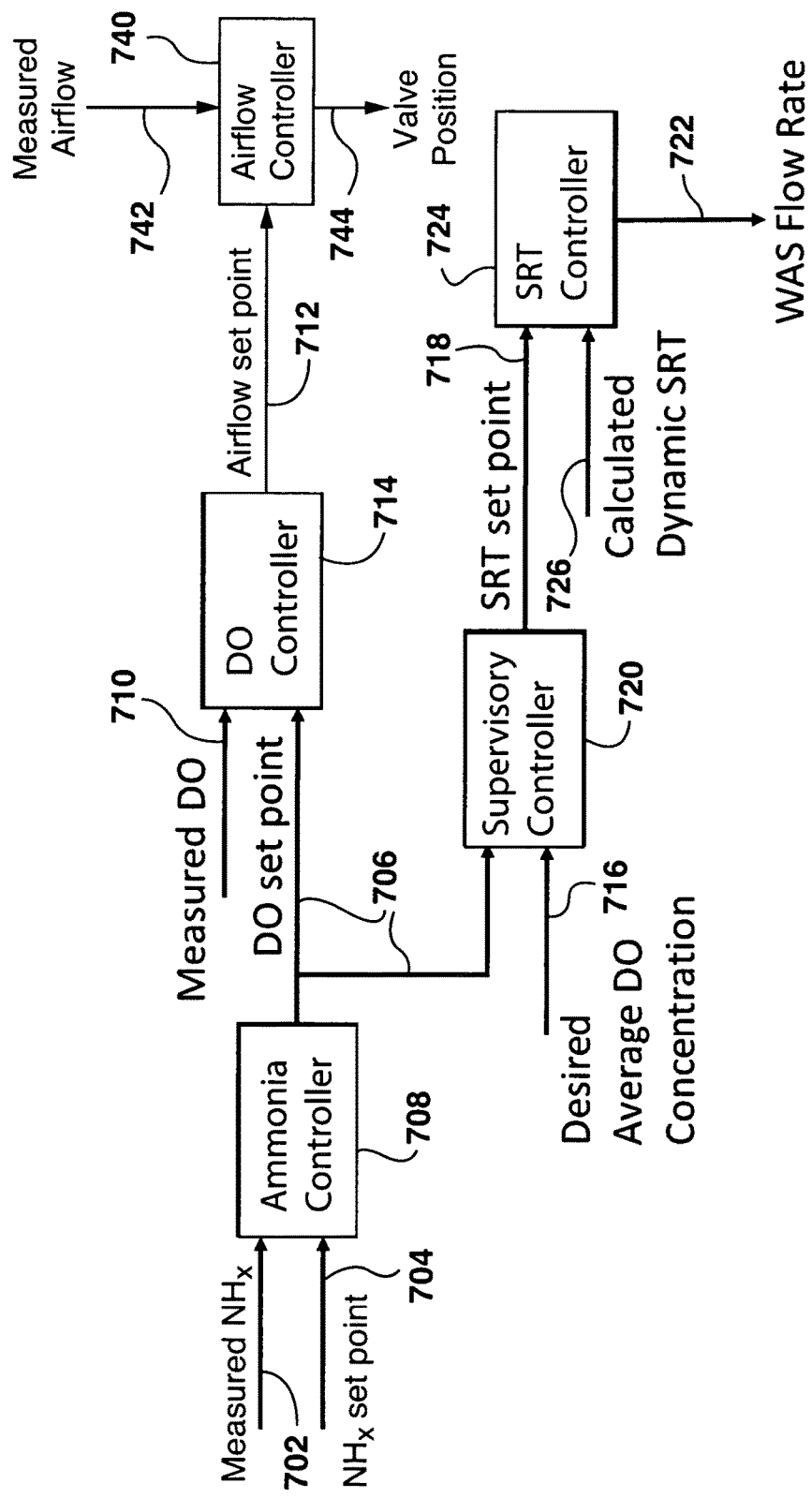
FIG. 7 is a schematic diagram showing an exemplary control concept for ammonia-based aeration control combined with SRT control.

The ABAC-SRT control concept is shown in FIG. 7, which is a schematic diagram showing an exemplary control concept for ammonia-based aeration control combined with SRT control. More particularly, FIG. 7 illustrates an exemplary method 700 of controlling aeration in an activated sludge-based water resource recovery facility. According to the method 700, the measured total ammonia nitrogen 702 in a volume of sludge in an aeration tank (e.g. aeration tank 122) is measured and compared to a target ammonia nitrogen setpoint 704 to calculate a target dissolved oxygen ("DO") setpoint 706 for adjusting the measured total ammonia nitrogen 702 toward the target ammonia nitrogen setpoint 704. In the illustrated embodiment, the target dissolved oxygen setpoint 706 is calculated by an ammonia controller 708. The measured dissolved oxygen 710 in the volume of sludge in the aeration tank is compared to the target dissolved oxygen setpoint 706 to calculate a target airflow setpoint 712 for adjusting the measured dissolved oxygen 710 toward the target dissolved oxygen setpoint 706. In the illustrated embodiment, the target airflow setpoint 712 is calculated by a dissolved oxygen controller 714. Airflow into the aeration tank is adjusted toward the target airflow setpoint 712. Adjustment of airflow into the aeration tank may be achieved by the dissolved oxygen controller 714 adjusting airflow directly by controlling at least one valve, or by the dissolved oxygen controller 714 sending the target airflow setpoint to an airflow controller 740 that controls 744 the valve and which receives feedback from a measured airflow 742. Thus, the ammonia controller 708 is a feedback controller that measures $NH_x$—N and manipulates the setpoint of the dissolved oxygen controller 714 which in turn manipulates the setpoint for an airflow controller, which may form part of the dissolved oxygen controller 714 or may be a separate controller.

The target dissolved oxygen setpoint 706 is also compared to a desired average dissolved oxygen concentration 716 to calculate a target solids retention time setpoint 718. In the illustrated embodiment, the target solids retention time setpoint 718 is calculated by a supervisory controller 720. The supervisory controller 720 is a feedback controller that controls the desired average dissolved oxygen concentration 716, which is a filtered or averaged version of the target dissolved oxygen setpoint 706 calculated by the ammonia controller 708. Averaging of the target average dissolved oxygen setpoint 706 calculated by the ammonia controller 708 is performed using a low-pass filter or moving average calculation. Thus, comparing the target dissolved oxygen setpoint 706 to the desired average dissolved oxygen concentration 716 may include pre-processing, such as filtering or averaging.

The target solids retention time setpoint 718 is used to adjust the solids retention time for the aeration tank toward the target solids retention time setpoint 718. The target solids retention time setpoint 718 may be used to adjust a waste activated sludge flow rate 722 to adjust the solids retention time for the aeration tank toward the target solids retention time setpoint 718. As described above, the waste activated sludge flow could be directly from the aeration tank, from a line coupling the aeration tank to a primary clarifier, or could be from a return activated sludge line coupled to a secondary clarifier. In the illustrated embodiment shown in FIG. 7, the supervisory controller 720 provides the target solids retention time setpoint 718 to a solids retention time ("SRT") controller 724. The SRT controller 724 compares the target solids retention time setpoint 718 to a calculated dynamic solids retention time 726 and adjusts the waste activated sludge flow rate 722 to try to align the calculated dynamic solids retention time 726 with the target solids retention time setpoint 718. Thus, the SRT controller controls the estimated dynamic SRT (Vaccari et al., 1985 and Takács and Patry, 2002) by manipulating the waste activated sludge (WAS) flow rate and the supervisory controller 720 manipulates the target solids retention time setpoint 718 provided to the SRT controller 724 to allow the ammonia controller 708 to achieve its goals in the face of constraints on minimum airflows or the nitrifier population. The calculated dynamic solids retention time 726 may be obtained, for example, using Equation (1) above, by using Equation (5) above where F_p (mass flow of solids produced in the system) is calculated using Equation (6) above, or by any other suitable technique. A low-pass filter may be applied to the calculated dynamic solids retention time or to the measured or estimated quantities used in its calculation.

Optionally, in cases where there are a plurality of aeration tanks, adjusting the solids retention time for the aeration tanks toward the target solids retention time setpoint 718 may comprise temporarily ceasing inflow of wastewater to at least one of the plurality of aeration tanks, either in addition to or alternatively to adjustment of the waste activated sludge flow rate 722.

In some types of activated sludge-based water resource recovery facilities, nitrifying sludge, for example from a bio-augmentation tank, may be added to the aeration tank(s). In such cases, the calculations for adjusting the solids retention time for the aeration tank(s) toward the target solids retention time setpoint would account for addition of the nitrifying sludge; adaptation of the calculations is within the capability of one skilled in the art, now informed by the present disclosure.

Figure 8:
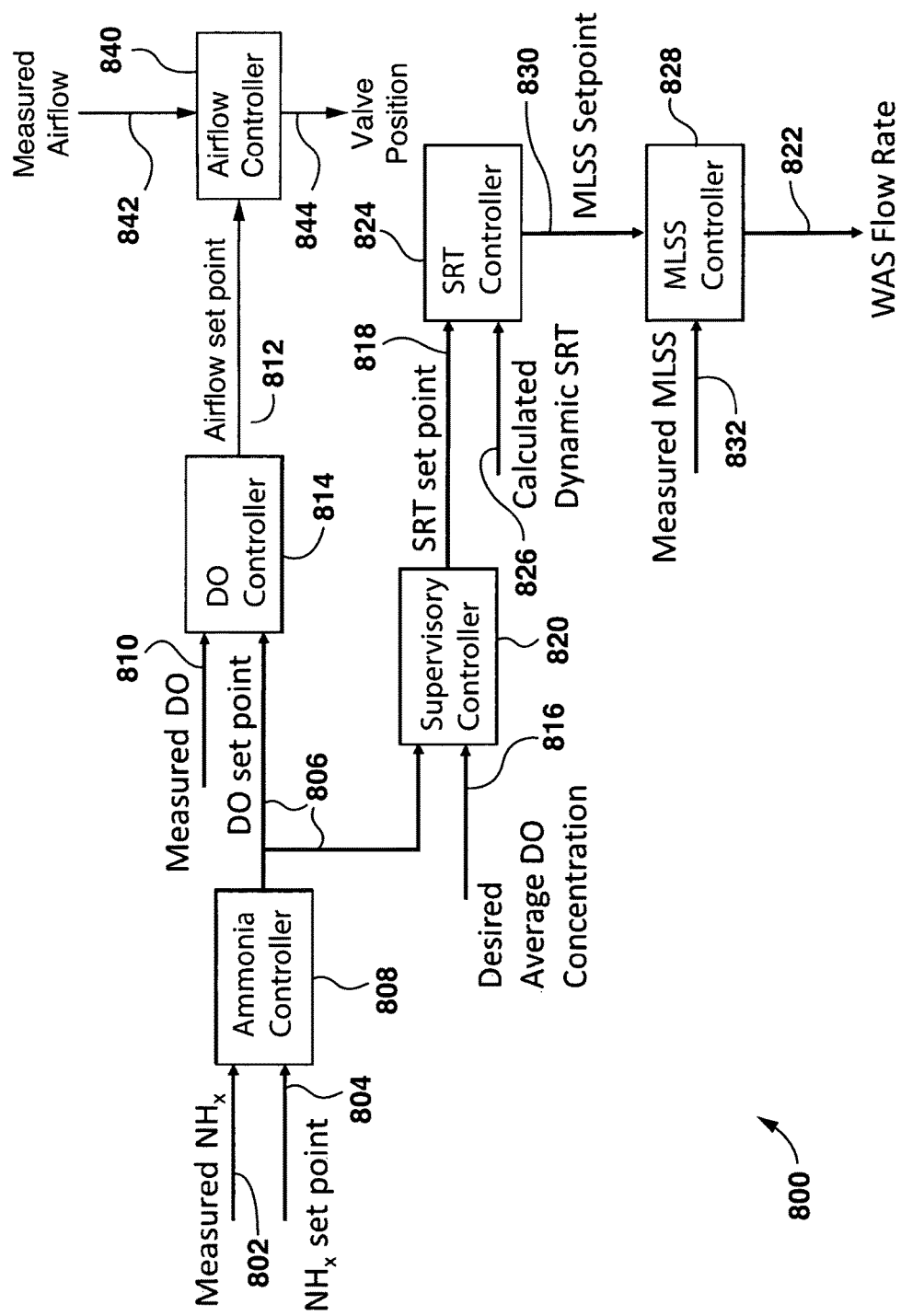
FIG. 8 is a schematic diagram showing an exemplary control concept for ammonia-based aeration control combined with SRT control combined with MLSS control of the WAS flow rate.

An important consideration is the selection of output bounds for the SRT controller. At low WAS flows, the resulting mixed liquor suspended solids ("MLSS") could be too high and cause clarifier failure. Reference is now made to FIG. 8, which is a modified version of the system shown in FIG. 7, with like reference numerals denoting like features except with the prefix "8" instead of "7". To assist in maintaining the MLSS in an acceptable range, the SRT controller 824 cascades to an MLSS controller 828 which has bounds on the mixed liquor suspended solids. More particularly, in the embodiment shown in FIG. 8, the SRT controller 824 compares the target solids retention time setpoint 818 to a calculated dynamic solids retention time 826 to calculate a target mixed liquor suspended solids (MLSS) setpoint 830, which is provided to the MLSS controller 828. The mixed liquor suspended solids concentration 832 in the aeration tank is measured, and the measured mixed liquor suspended solids concentration 832 is also provided to the MLSS controller 828. The MLSS controller 828 compares the measured mixed liquor suspended solids concentration 832 to the target mixed liquor suspended solids setpoint 830 to calculate the target waste activated sludge flow rate setpoint 822. The waste activated sludge flow rate for the aeration tank is then adjusted toward the target waste activated sludge flow rate setpoint 822.

The ABAC-SRT control concept was implemented in SIMBA#water and applied to the example WRRF introduced earlier. A year-long simulation was conducted in SIMBA#water with 12 storm events and seasonal temperature variation (air and wastewater). The wastewater temperature varies between 12.4° C. and 24° C., and the air temperature varies between −7.1° C. and 23.6° C. based on data taken from a wastewater treatment plant in Ontario, Canada. The temperature data show a delay of almost two months between the air and wastewater temperatures as changes in air temperature take time to affect the wastewater temperature.

To demonstrate the benefits of ABAC-SRT control, three cases are compared: Case 1: DO control with MLSS control, Case 2: ABAC with MLSS control, and Case 3: ABAC-SRT. For the DO control and ABAC options, the MLSS is controlled using a proportional-integral (PI) controller with a setpoint of 2,000 mg/L. MLSS control is used in Cases 1 and 2 as it is thought to represent a common control strategy at many WRRFs due to concerns about clarifier failure at high MLSS concentrations. The supervisory controller has minimum and maximum output bounds of 3 days and 20 days respectively to impose bounds on the SRT setpoint. The SRT controller has MLSS bounds of between 1,000 and 3,500 mg/L. The simulated scenarios are summarised in Table 1.

TABLE 1

Simulated Scenarios

| Scenario | Airflow control | DO control | $NH_x$-N control | MLSS control | SRT control | Supervisory Control |
|---|---|---|---|---|---|---|
| Case 1 | Airflow setpoint provided by DO controller for each zone | DO setpoint of 2 mg/L in all zones | Not used | MLSS setpoint = 2,000 mg/L WAS flow rate bounded between 100 and 3,500 m³/d | Not used | Not used |
| Case 2 | Airflow setpoint provided by DO controller for each zone | DO setpoint provided by $NH_x$-N controller Airflow setpoint bounded between minimum airflow for mixing and maximum airflow per diffuser | $NH_x$-N setpoint = 1 mg/L DO setpoint bounded between 0.5 and 2 mg/L | MLSS setpoint = 2,000 mg/L WAS flow rate bounded between 100 and 3,500 m³/d | Not used | Not used |
| Case 3 | Airflow setpoint provided by DO controller for each zone | DO setpoint provided by $NH_x$-N controller Airflow setpoint bounded | $NH_x$-N setpoint = 1 mg/L DO setpoint bounded between | MLSS setpoint provided by SRT controller WAS flow rate | SRT setpoint provided by supervisory controller MLSS setpoint | Average DO setpoint for supervisory controller of 1 mg/L SRT |

TABLE 1-continued

Simulated Scenarios

| Scenario | Airflow control | DO control | $NH_x$-N control | MLSS control | SRT control | Supervisory Control |
|---|---|---|---|---|---|---|
| | | between minimum airflow for mixing and maximum airflow per diffuser | 0.5 and 2 mg/L | bounded between 100 and 3,500 m³/d | bounded between 1,000 and 3,500 mg/L | setpoint bounded between 3 and 20 days |

In Case 1, the $NH_x$—N is uncontrolled and over-aeration is possible. In Cases 2 and 3, the $NH_x$—N setpoint in the $3^{rd}$ bioreactor is set to 1 mgN/L in order to achieve potential energy savings. The airflow controllers are bounded between 0.22 $Nm^3/h$ per $m^2$ of floor area (0.12 $scfm/ft^2$ based on USEPA, 1989) and 14 $Nm^3/h$ per diffuser (7.6 scfm/diffuser) to provide adequate airflow for mixing and to remain within the upper airflow limit for the diffusers. The DO setpoint calculated by the ammonia controller is bounded between 0.5 mg/L (to prevent extended operation at low DO concentrations in cases without SRT control) and 2 mg/L (to prevent excessive aeration). The ammonia controller is a proportional-integral-derivative (PID) controller and all the remaining controllers are proportional-integral (PI) controllers.

Figure 9:
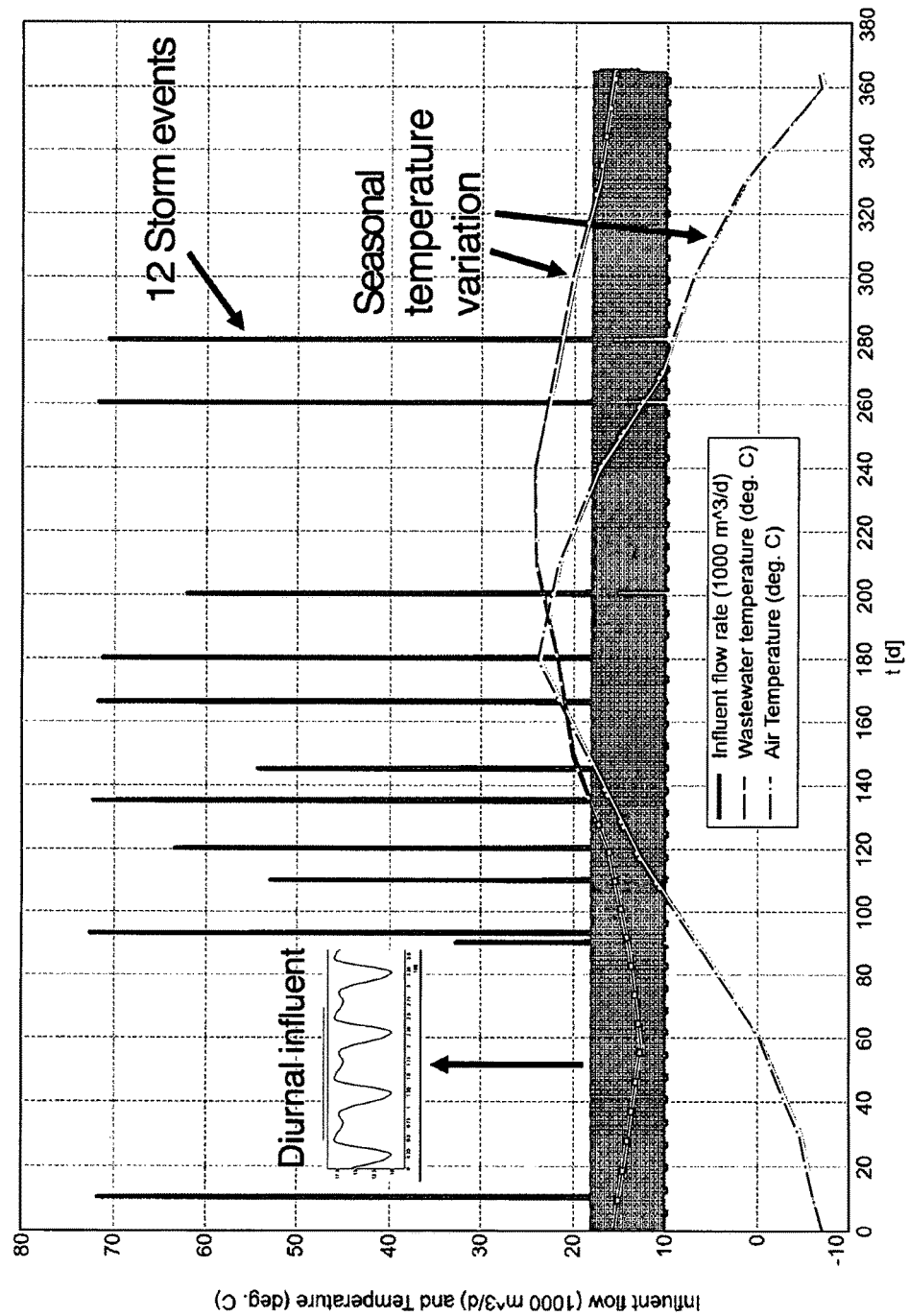
FIG. 9 is a graph showing a diurnal flow pattern including 12 storm events, seasonal liquid temperature pattern, and seasonal air temperature pattern for a 365 day simulation.
Figure 10A:
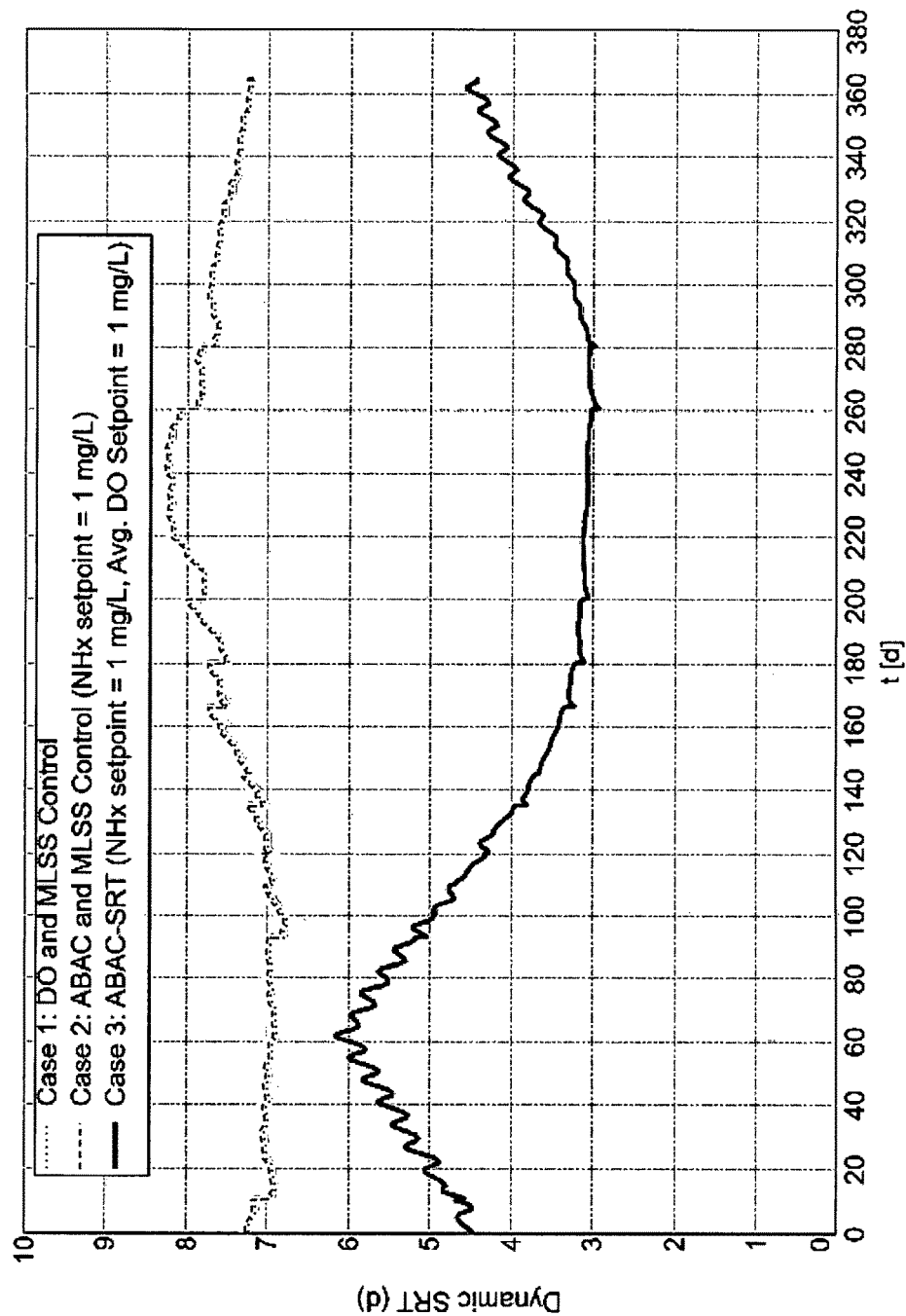
FIG. 10A is a graph showing a simulated dynamic SRT for DO and MLSS control, ABAC and MLSS control and ABAC-SRT control.
Figure 10B:
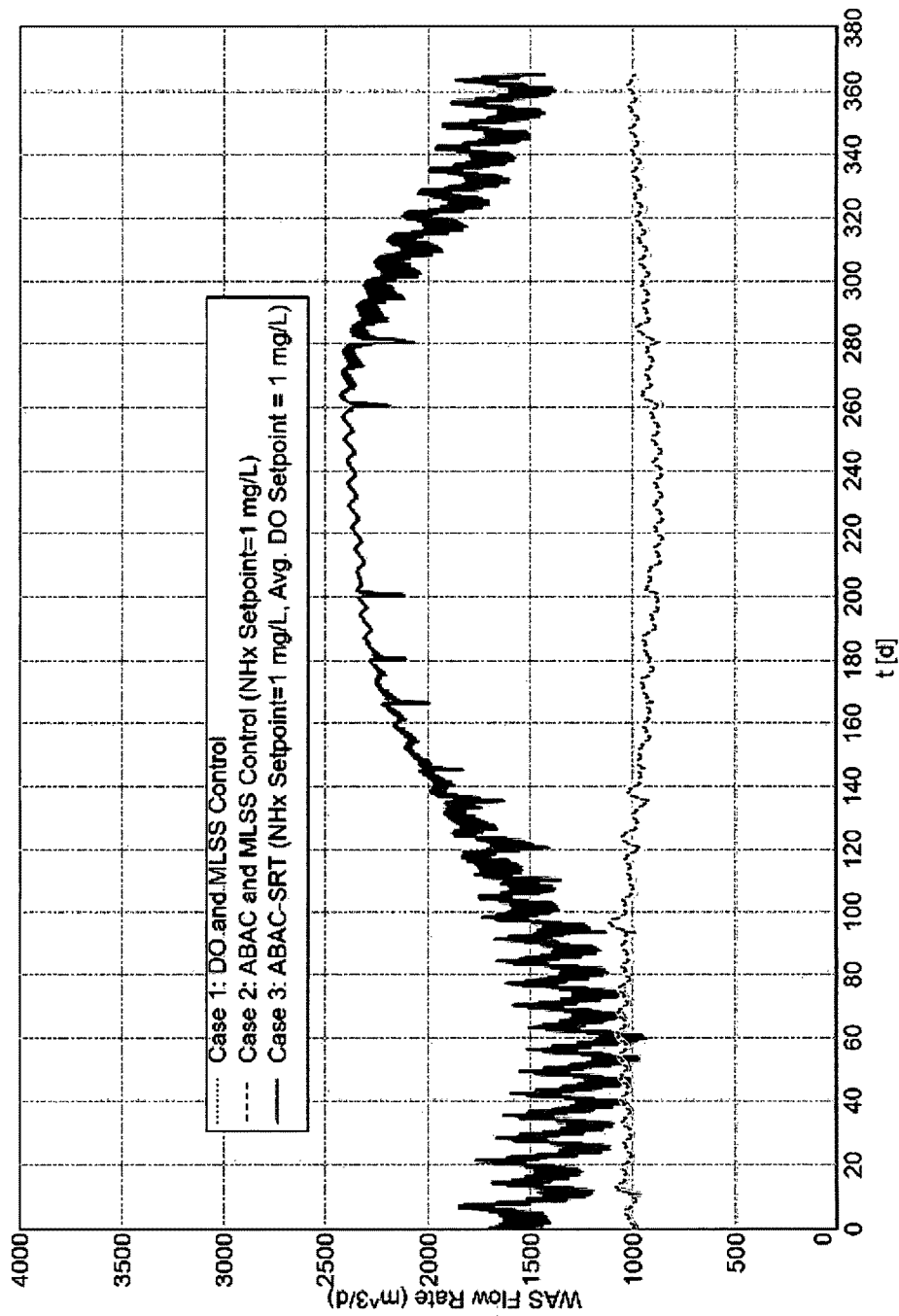
FIG. 10B is a graph showing a simulated dynamic WAS flow rate for DO and MLSS control, ABAC and MLSS control and ABAC-SRT control.

The year-long influent flow, air, and wastewater temperature patterns are shown in FIG. 9. FIGS. 10A and 10B show the resulting simulated dynamic SRT (controlled variable) and the WAS flow rate (manipulated variable), respectively, for Case 1 (DO control with MLSS control), Case 2 (ABAC with MLSS control), and Case 3 (ABAC-SRT control). As shown, in Case 3 the WAS flow rate is adjusted so that the SRT varies throughout the year. The SRT variation follows the wastewater temperature variation. The lower SRT and MLSS bounds of 3 days and 1,000 mg/L respectively become active during the warmer months.

Figure 11A:
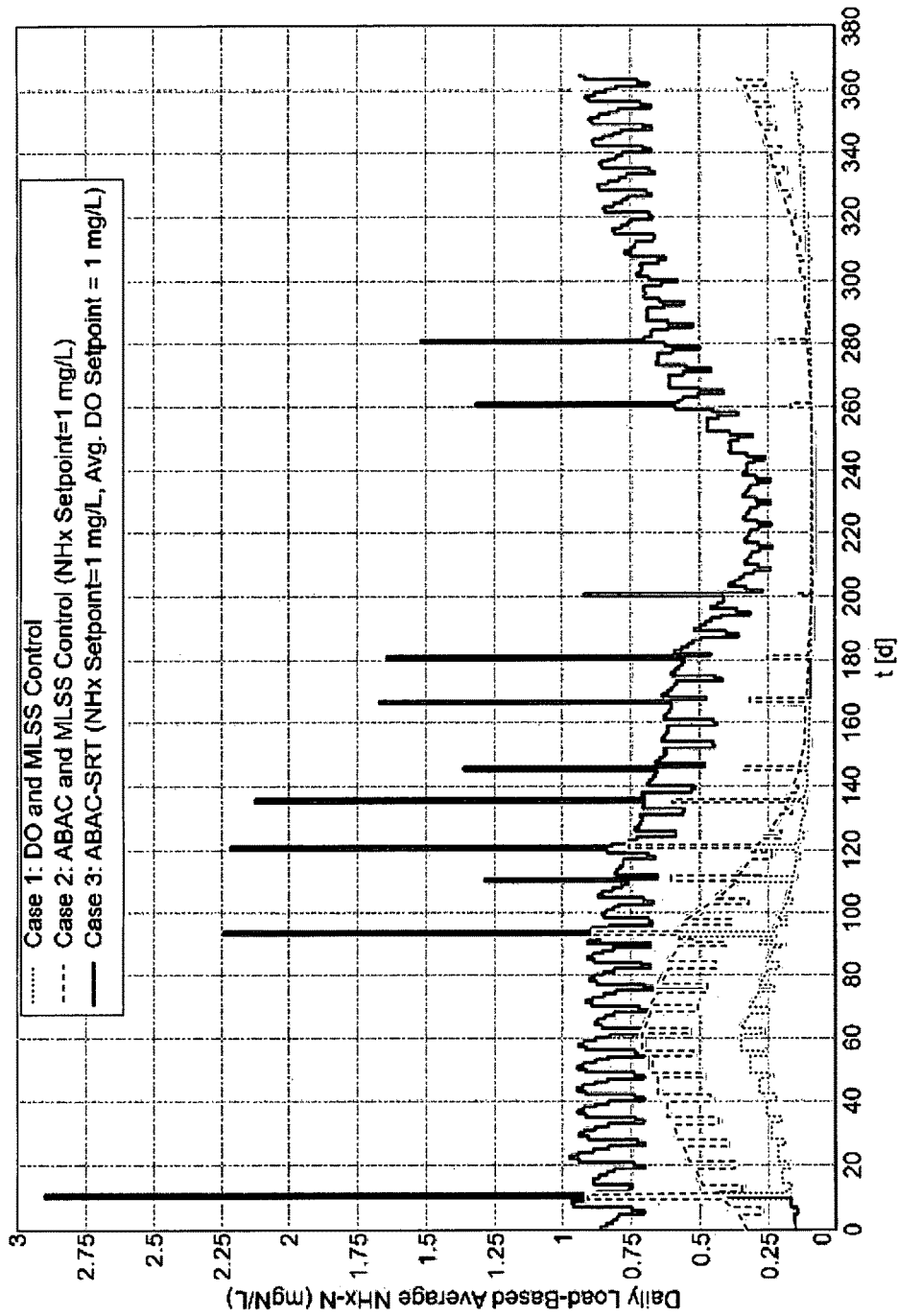
FIG. 11A is a graph showing simulated load-based average $NH_x$—N in $3^{rd}$ bioreactor SRT for DO and MLSS control, ABAC and MLSS control and ABAC-SRT control.
Figure 11B:
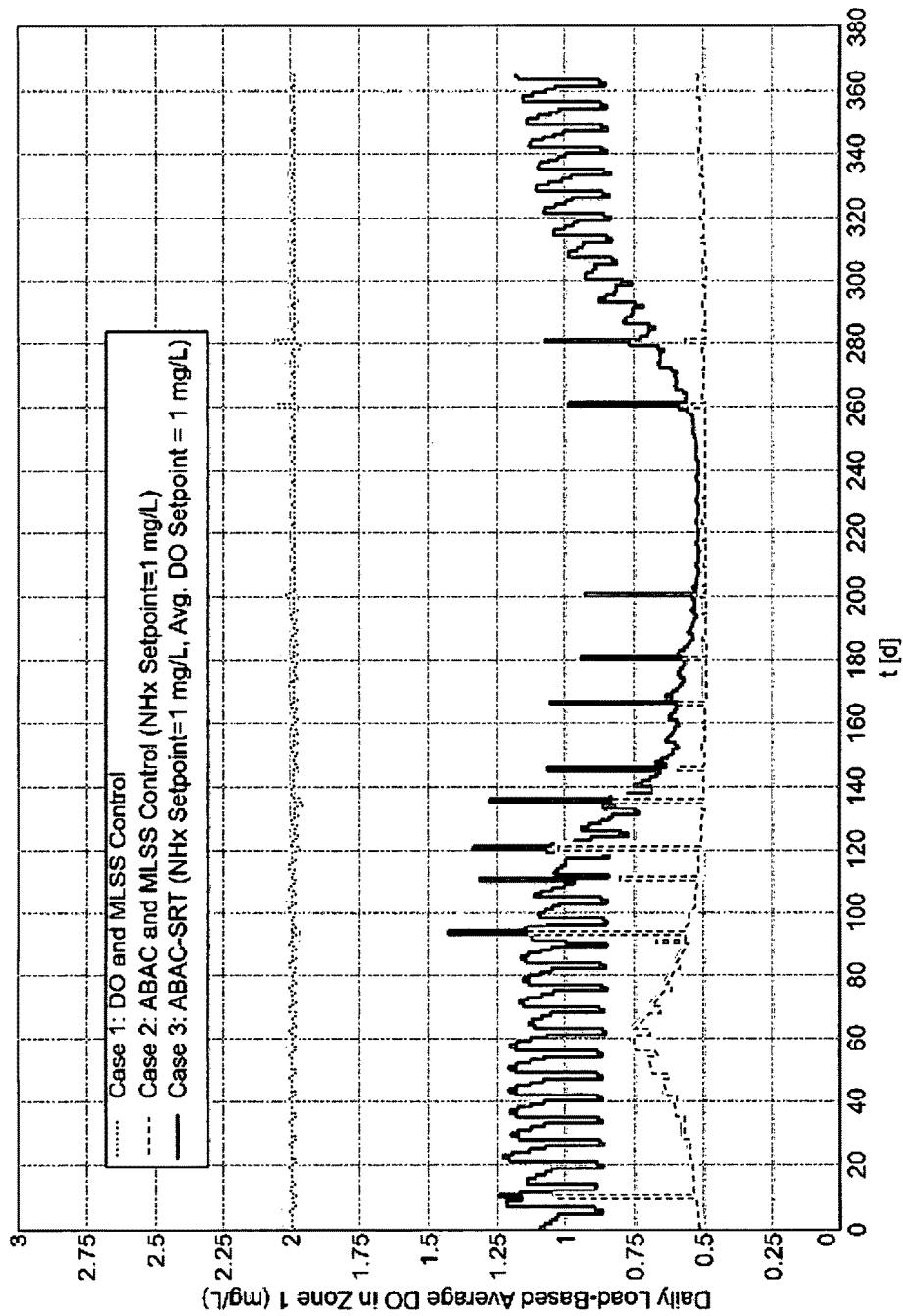
FIG. 11B is a graph showing simulated load-based average $NH_x$—N in Zone 1 DO for DO and MLSS control, ABAC and MLSS control and ABAC-SRT control.

FIGS. 11A and 11B show the load-based average $NH_x$—N in the $3^{rd}$ bioreactor (controlled variable) and the load-based average DO in the $1^{st}$ bioreactor (manipulated variable), respectively. In all three cases, the ammonia-controller cannot keep the daily average Zone 3 $NH_x$—N at the setpoint of 1 mgN/L at all times. In Case 1, this is because a DO of 2 mg/L is maintained in all three zones which is sufficient for full nitrification at the operating SRT (7 days and above). In Case 2, the ammonia controller reaches its lower DO bound of 0.5 mg/L, but the DO in the last zone is consistently above 2 mg/L because of the minimum airflow bound for mixing. At the SRTs encountered, this is enough to keep the daily average Zone 3 significantly below the 1 mgN/L setpoint. The ABAC-SRT controller performs the best in terms of achieving the $NH_x$—N setpoint because of the supervisory control of the SRT setpoint.

The ABAC-SRT control concept enables the SRT to be long enough to attenuate peak loads while at the same time inhibiting aeration system constraints from limiting control authority. Despite this, ABAC-SRT can still be limited to some extent by the bounds on SRT, MLSS, and DO setpoints which provide a measure of safety. These setpoint bounds can be fine-tuned to allow unconstrained operation of the control system if desired.

Figure 12:
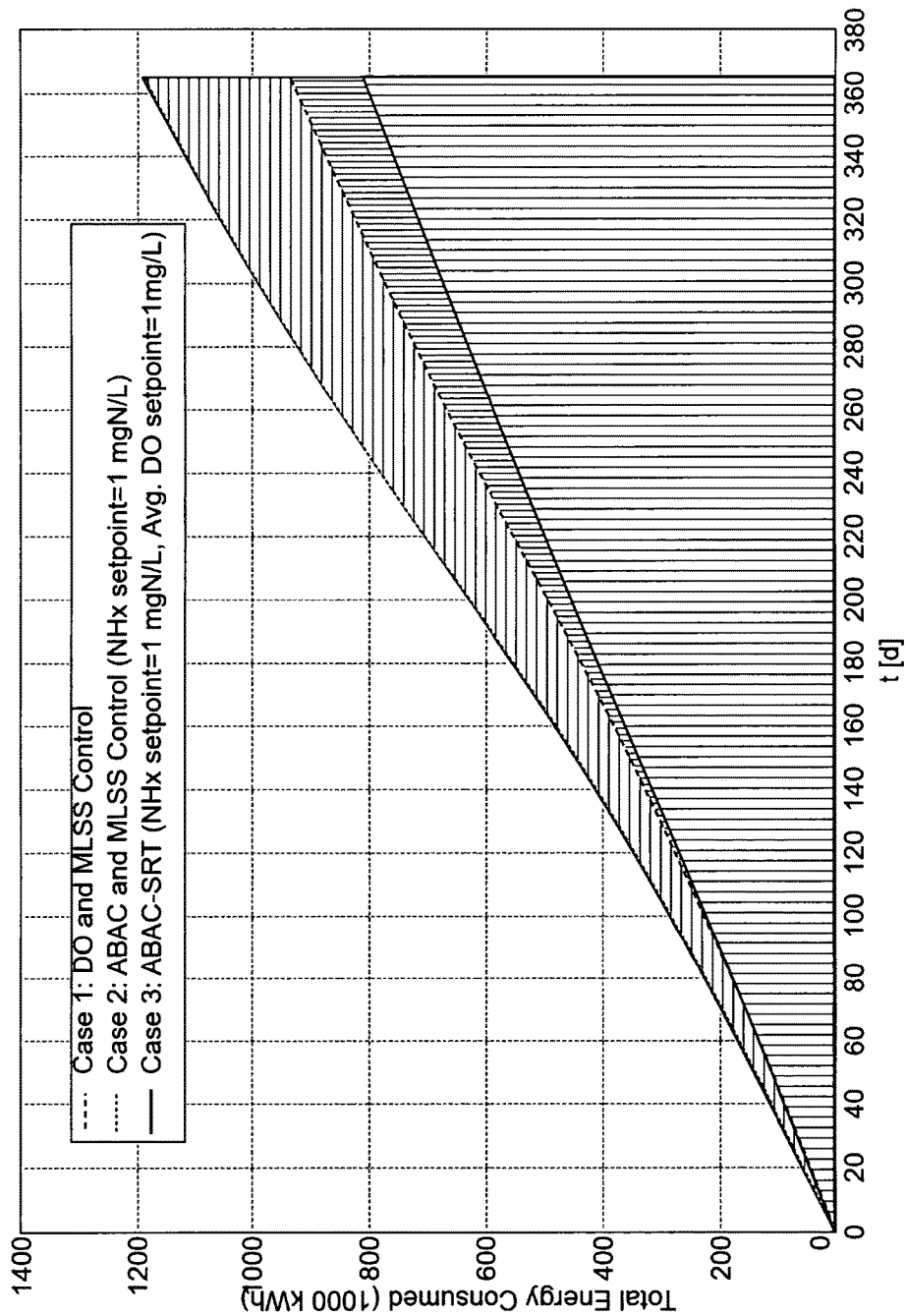
FIG. 12 is a graph showing simulated cumulative energy consumption for DO and MLSS control, ABAC and MLSS control and ABAC-SRT control.

Aeration energy consumption was calculated for the three cases and was 3,260 kWh/d for Case 1 (DO and MLSS control), 2,550 kWh/d for Case 2 (ABAC with MLSS control), and 2,220 kWh/d for Case 3 (ABAC-SRT control). FIG. 12 shows cumulative energy consumption for the entire simulation for the three cases. The Case 2 (ABAC with MLSS control) strategy results in a 22% reduction in energy consumption as compared to Case 1 (DO and MLSS control). This energy reduction is consistent with that reported by Amand et al. (2013) and Rieger et al. (2012) for full-scale WRRFs that implemented ABAC.

The Case 3 (ABAC-SRT control) strategy results in a 32% reduction in energy consumption as compared to Case 1 (DO and MLSS control), an additional 10% in energy savings, relative to Case 2 (ABAC with MLSS control), due to SRT setpoint adjustment. Another potential benefit of the ABAC-SRT strategy is a lower mixed liquor suspended solids (MLSS) concentration which helps reduce solids loss during storms for plants operated at high MLSS concentrations. As shown, the level of savings with ABAC and ABAC-SRT depends on the $NH_x$—N setpoint. They are also impacted by the lower bound on the DO setpoint and in the case of ABAC-SRT on the lower bound on the SRT and MLSS setpoints.

Figure 13:
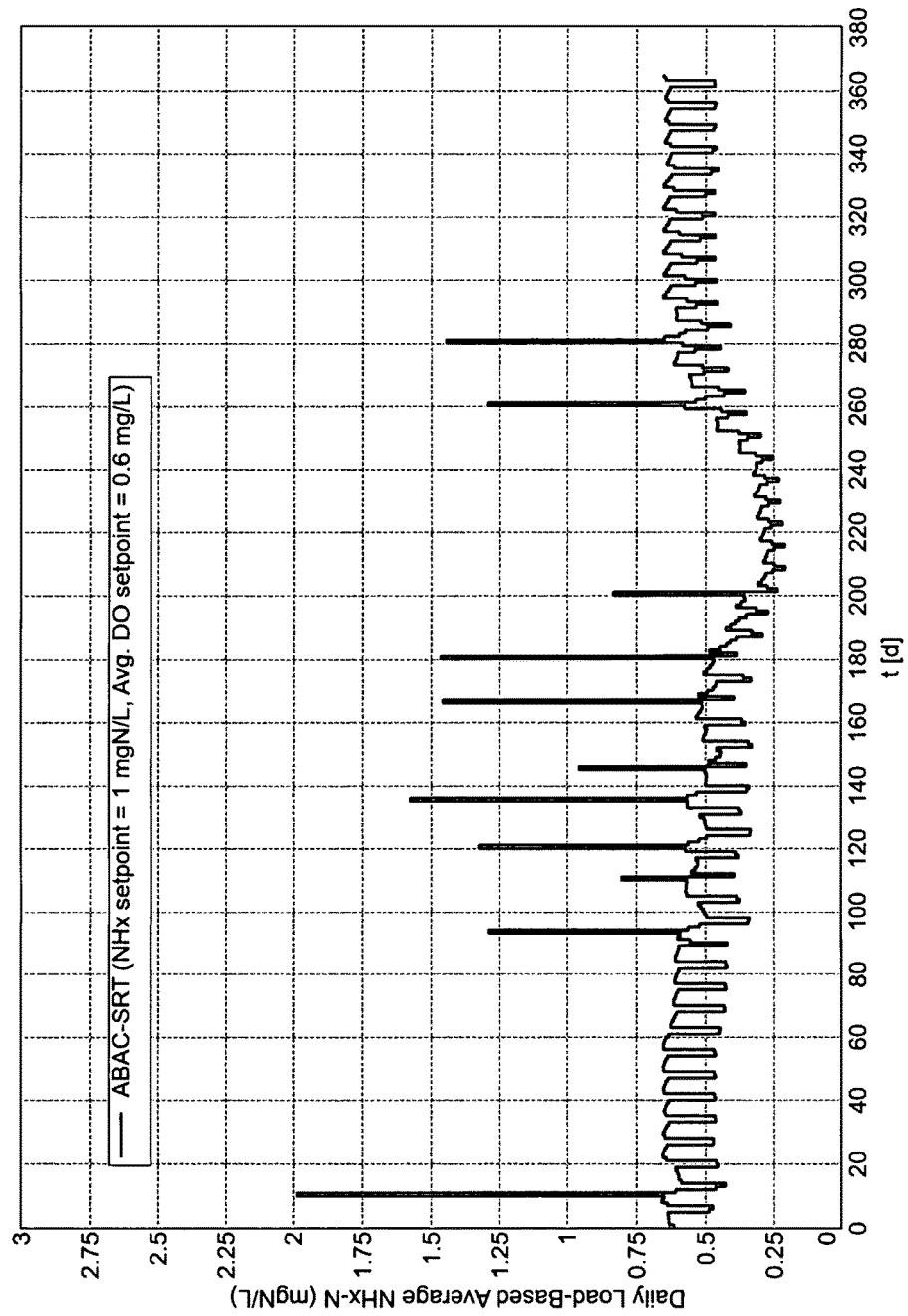
FIG. 13 is a graph showing simulated load-based average $NH_x$—N in 3rd bioreactor with average DO setpoint for supervisory controller set to 0.6 mg/L.

An important consideration when implementing ABAC-SRT is the selection of the average DO setpoint of the supervisory controller. In the case study discussed earlier, the average DO setpoint of the supervisory controller was 1 mg/L. FIG. 13 shows the impact on the controlled $NH_x$—N when the average DO setpoint is changed to 0.6 mg/L. As shown, the average DO setpoint determines whether the SRT is in the correct range so that the ammonia controller can function properly to inhibit $NH_x$—N break-through and to support energy savings.

Another implementation issue is the selection of the time interval ($\Delta t$) used in Equation 6. Longer time intervals serve to filter the impact of diurnal variations on the calculation of the sludge production and the impact of solids being pushed into the clarifiers during storms. If $\Delta t$ is too small, the dynamic SRT will vary considerably in response to diurnal variations (although not as much as the static SRT) and will be incorrectly impacted by solids being pushed into the clarifiers during a storm (as the solids are temporarily lost as far as the calculation is concerned unless the solids mass in the clarifier is tracked). A time interval of one day in Equation 6 was found to provide a reasonable compromise between accuracy and eliminating the negative impact of high frequency flow variations.

Proper controller tuning is also important for the ABAC-SRT control strategy. The system contains a number of cascaded controllers that could exhibit poor performance if not tuned properly. The lowest loops in the cascade (i.e. airflow controllers and the MLSS controller) should be tuned for a faster response than the loops higher in the cascade and could be proportional-only controllers. As a starting point for tuning the controller tuning constants, tuning correlations such as Ciancone and Marlin (1992) can be used. Use of tuning correlations requires knowledge of the process gain, time constant, and transportation lag for each control loop which can be determined using a simulation model or plant step-response tests.

In the SIMBA#water model used in this study, the controllers were fine-tuned by introducing step changes in the controller setpoints and adjusting the tuning constants to achieve the desired dynamic response. The MLSS and SRT controllers were tuned for a slow dynamic response so that the WAS flow variations were not overly aggressive. The controller integral times are on the order of days for the SRT-related controllers and on the order of minutes for the ammonia, DO, and air flow controllers. The SRT-related controller gains depend on the SRT range that the system is operating within, suggesting that gain scheduling could be beneficial although this was not tested during this study.

In Case 3 (ABAC-SRT control), the goal of the supervisory controller was to keep the average DO at 1 mg/L. This is achieved during the colder months but the average DO drops lower than 1 mg/L in the warmer months because of the minimum SRT bound of 3 days. This leads to the daily average Zone 3 $NH_x$—N to drop lower than the setpoint.

The ABAC-SRT systems and methods described herein can be applied to sequencing batch reactors as well. In a sequencing batch reactor (SBR), the wastewater processing steps of an activated sludge plant are done in one semi-batch tank that has filling, mixing, reaction, settling, decanting and idle phases.

Figure 15:
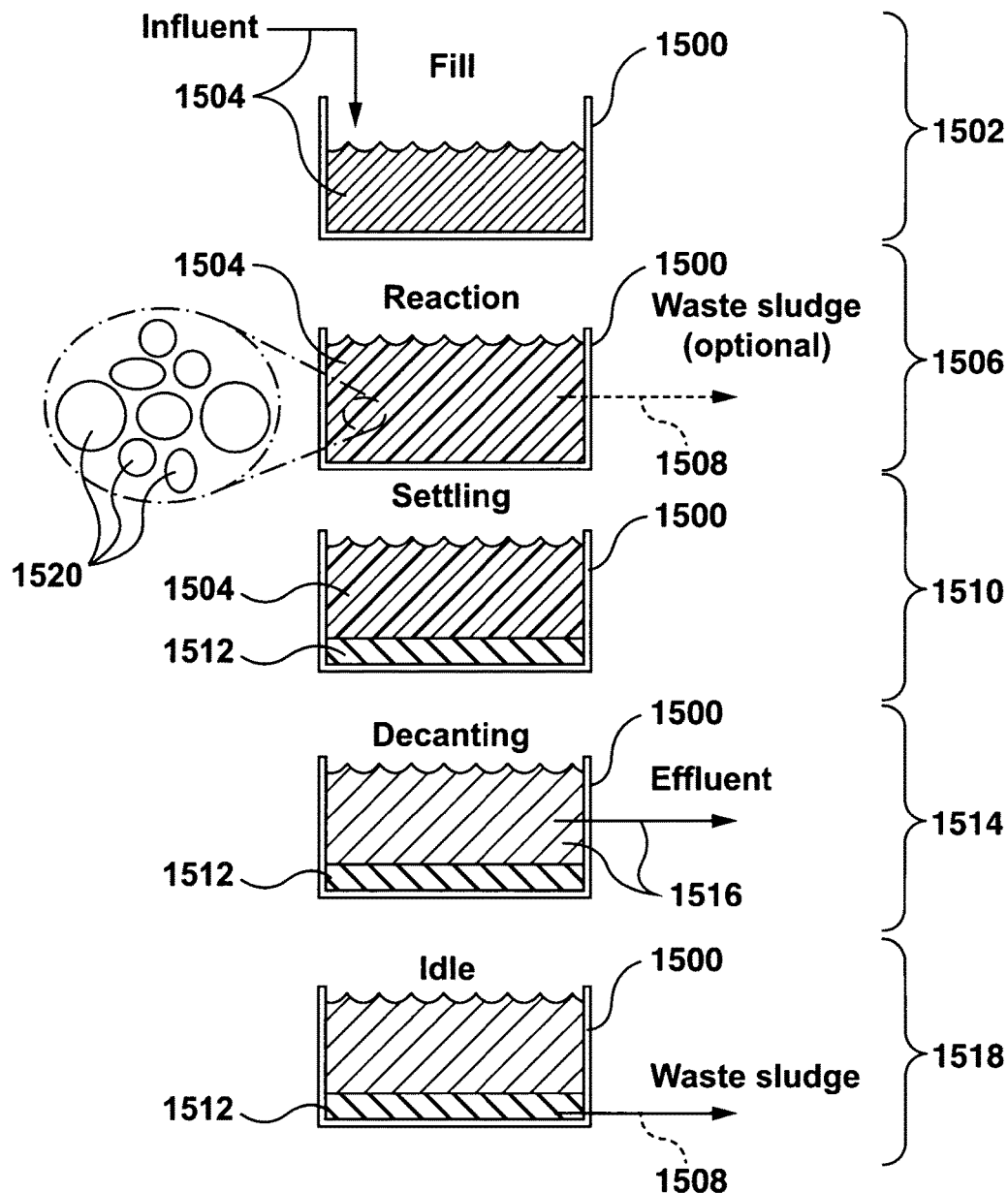
FIG. 15 is a schematic diagram showing the operational phases of an SBR tank.

Reference is now made to FIG. 15, which is a schematic diagram showing the operational phases of an SBR tank, indicated by reference 1500. During a fill phase 1502, influent wastewater 1504 is added to the tank 1500; no aeration takes place during the fill phase 1502. Next, during a reaction phase 1506, the wastewater 1504 is mixed with air and bacteria. The air is introduced using blowers that force air through pipes that feed diffusers within the tank 1500. The wastewater 1504 remains in the tank 1500 while the bacteria consume the organic matter contained in the wastewater 1504. The aeration can be on for the entire duration of the reaction phase 1506, or only a portion of the reaction phase 1506. Optionally, waste sludge 1508 may be drawn out of the tank 1500 during the reaction phase 1506. The reaction phase 1506 is followed by a settling phase 1510, during which sludge 1512 is permitted to settle to the bottom of the tank 1500, which is in turn followed by a decanting phase 1514 during which effluent 1516, i.e. treated wastewater, is drawn out of the tank 1500. There is no aeration during the settling phase 1510 or during the decanting phase 1514. After completion of the decanting phase 1514, the tank 1500 is in an idle phase 1518 during which waste sludge 1508 may be drawn out of the tank 1500; thus, wasting can be done during either the reaction phase 1506 or during the idle phase 1518. Aeration can optionally take place during the idle phase 1518.

In an SBR, the SRT is a function of the waste activated sludge flow rate but aerobic phase length within each cycle determines the aerobic SRT. ABAC-SRT systems and methods described herein can be applied to SBRs by adjusting the length of the aerobic phase, i.e. the length of the aerated portion of the reaction phase instead of (or in addition to) adjusting the dissolved oxygen setpoint. This process will now be described with reference to FIG. 16.

Figure 16:
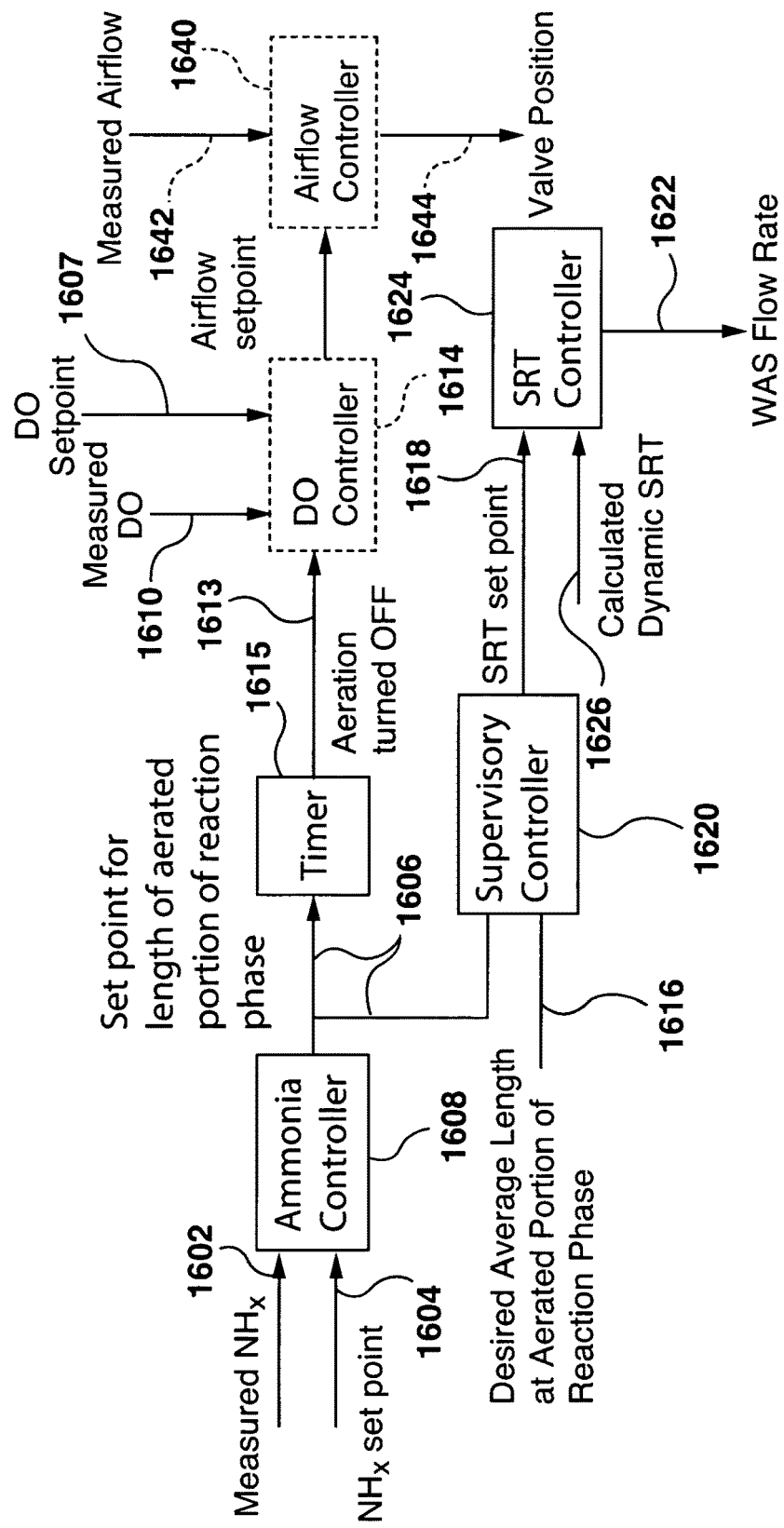
FIG. 16 is a schematic diagram showing an exemplary control concept for ammonia-based aeration control combined with SRT control as applied in the SBR context.

FIG. 16 is similar to FIG. 7, and is a schematic diagram that shows an exemplary control concept for ammonia-based aeration control combined with SRT control as applied in the SBR context. Thus, FIG. 16 illustrates a method of supervisory control for an activated sludge-based water resource recovery facility comprising at least one SBR. According to the method 1600, for at least one SBR in the water resource recovery facility, the measured total ammonia nitrogen 1602 in a volume of sludge in the SBR is measured during an aerobic phase of the SBR and compared to a target ammonia nitrogen setpoint 1604 to calculate a target aerobic phase length 1606 for adjusting the measured total ammonia nitrogen 1602 toward the target ammonia nitrogen setpoint 1604. The method 1600 then adjusts the duration of airflow into the at least one SBR toward the target aerobic phase length 1606. In the illustrated embodiment, the target aerobic phase length 1606 is calculated by an ammonia controller 1608 and fed to a timer 1615 which controls when the airflow into the SBR is turned off 1613 (i.e. when the aeration portion of the reaction phase ends). The timer 1615 may be integrated into the ammonia controller 1608, i.e. the ammonia controller 1608 can function as an on/off controller or timer for the aeration system. Thus, the ammonia controller 1608 now controls the ammonia during the aerobic phase by adjusting the length of the aerobic portion of the reaction phase. As soon as the ammonia falls below the set point, the ammonia controller 1608 stops the aerobic portion of the reaction phase. In some embodiments, a constant airflow rate is provided during the aeration portion of the reaction phase. Optionally, a dissolved oxygen ("DO") controller 1614 receiving a DO setpoint 1607 and measured DO readings 1610 and outputting an airflow setpoint 1612 to an airflow controller 1640 receiving measured airflow readings 1642, may be integrated into the system to provide for tuning of the airflow rate, in addition to controlling its duration, by the airflow controller 1640 adjusting a valve position 1644.

In the exemplary implementation of the method 1600 shown in FIG. 16, the target aerobic phase length 1606 is used to adjust a target solids retention time (SRT) setpoint 1618, and the waste activated sludge flow rate 1622 for the SBR during the aerobic phase is adjusted according to the solids retention time setpoint 1618. In the illustrated embodiment, the target solids retention time setpoint 1618 is calculated by a supervisory controller 1620. The supervisory controller 1620 is a feedback controller that controls the desired average length of the aerated portion of the reaction phase 1616, and determines a suitable solids retention time setpoint 1618 in the context of the desired average length of the aerated portion of the reaction phase 1616. The target solids retention time setpoint 1618 is used to adjust the waste activated sludge flow rate 1622 to adjust the solids retention time for the aeration tank toward the target solids retention time setpoint 1618. In the illustrated embodiment shown in FIG. 16, the supervisory controller 1620 provides the target solids retention time setpoint 1618 to a solids retention time ("SRT") controller 1624. The SRT controller 1624 compares the target solids retention time setpoint 1618 to a calculated dynamic solids retention time 1626 and adjusts the waste activated sludge flow rate 1622 to try to align the calculated dynamic solids retention time 1626 with the target solids retention time setpoint 1618. In other words, the supervisory controller 1620 now controls the average aerated phase length by adjusting the target solids retention time setpoint 1618. The supervisory controller 1620 has an average aerated phase length set point (i.e. the desired average length of the aerated portion of the reaction phase 1616) and compares this to the target aerobic phase length 1606 (a filtered aerated phase length) outputted by the ammonia controller 1608. As in the system shown in FIG. 7, the SRT controller 1624 adjusts the waste activated sludge flow rate 1622, but during the aerated portion of the reaction phase 1616 or during the idle phase 1518.

One skilled in the art, now informed by the present disclosure, will appreciate that the approach described above with respect to SBRs may also be applied, mutatis mutandis, to conventional activated sludge plants that use intermittent aeration (i.e. aerate for a period, then stop aerating for a period, then repeat). In this case, the ammonia controller controls the length of the aeration period. Thus, with respect to the method 700 described above in FIG. 7 as applied to an activated sludge-based water resource recovery facility in which the airflow is intermittent, adjusting airflow into the aeration tank(s) toward the target airflow setpoint may comprise adjusting aeration period length (and optionally adjusting airflow) to adjust the ammonia nitrogen toward the target ammonia nitrogen setpoint.

Each of the ammonia controller 708, 808, 1608, the dissolved oxygen controller 714, 814, 1614, the supervisory controller 720, 820, 1620, the solids retention time controller 724, 824, 1624 and the mixed liquor suspended solids controller 828, as well as the airflow controller(s) 740, 840, 1640, may be a distinct individual programmable logic controller, or a software module executing in at least one processor of a computer, or a combination of the foregoing.

The systems and methods described herein, whether for conventional activated sludge plants (with or without intermittent aeration) or for SBRs, can be applied to granular sludge reactors, in which the aeration tanks contain granular sludge as opposed to flocculated sludge and granules are defined as compact microbial aggregates that settle significantly faster than activated sludge flocs with settling velocities greater than 9 m/h. Granular sludge reactors cultivate large granules of bacteria as compared to the flocs that form in conventional activated sludge systems. The granules are larger and denser than activated sludge flocs. The advantage is that many different organisms can co-exist in the granules, can perform multiple processes in parallel, and that the granules settle well allowing high bacterial concentrations within the reactors. This is another way of intensifying treatment. SBRs are the most common type of reactor used in this context, and as shown in FIG. 15, in the illustrated embodiment the SBR tank 1500 contains a plurality of granules 1520 of granular sludge. The granules 1520 are encouraged to form by having short settling times and high shear stresses so that detachment rate of bacteria from the granules is high compared to the growth rate of the organisms. The characteristics of the wastewater are thought to be important as well. Without being limited by theory, feeding soluble readily biodegradable substrate is thought to help facilitate the formation of granular sludge. Thus, the aeration tanks 122 or the SBR tank 1500 may contain flocculated sludge or granulated sludge or a combination of the two.

Figure 17:
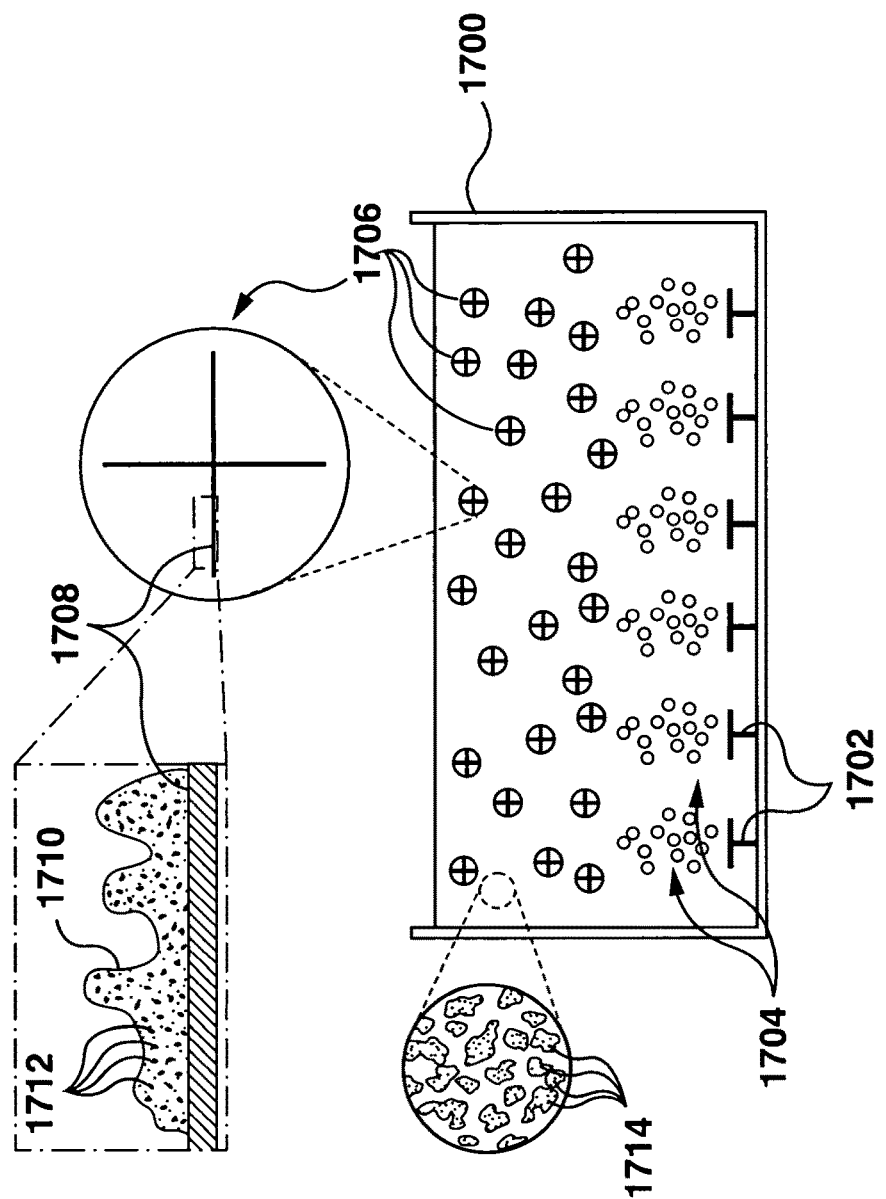
FIG. 17 is a schematic drawing of an exemplary IFAS aeration tank.

The systems and methods described herein can also be applied to integrated fixed-film activated sludge reactors (IFAS) in which support media (e.g. made from a suitable plastic) are disposed within the aeration tank(s), with the support media being adapted to allow biofilm growth thereon. The support media can be fixed in place or float within the tank, and bacteria grow on the media in addition to growing in the liquid phase. The media serve to increase the mass of bacteria within the aeration tank without increasing its volume thereby intensifying treatment and allowing an increase in plant capacity. FIG. 17 is a schematic drawing of an exemplary IFAS aeration tank 1700, which may be part of either a conventional activated sludge plant or an SBR. The IFAS aeration tank 1700 has a plurality of diffusers 1702 disposed at the bottom thereof, which provide course bubble aeration 1704. In the illustrated embodiments, the support media comprise plastic carriers 1706 that float within the IFAS aeration tank 1700 and provide surfaces 1708 on which a biofilm 1710 containing bacteria 1712 can accumulate. Activated sludge flocs 1714 are also present in the IFAS aeration tank 1700. The aeration tanks 122 or SBR tank 1500 may be IFAS reactors.

As can be seen from the above description, the ABAC-SRT systems and methods described herein represent significantly more than merely using categories to organize, store and transmit information and organizing information through mathematical correlations. The ABAC-SRT systems and methods are in fact an improvement to the technology of water resource recovery facilities, as they provide for effective coordination of the airflow setpoint and the solids retention time setpoint in a water resource recovery facility. This facilitates the ability of the control system of a water resource recovery facility to align the goals of ammonia-based aeration control and SRT control. The ABAC-SRT systems and methods have the potential to reduce aeration energy consumption compared to traditional DO control. Moreover, the ABAC-SRT technology is applied by using a particular apparatus, namely a water resource recovery facility. As such, the ABAC-SRT technology is confined to water resource recovery facility applications.

The present technology may be embodied within a system, a method, a computer program product or any combination thereof. The computer program product may include a computer readable storage medium or media having computer readable program instructions thereon for causing a processor to carry out aspects of the present technology. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing.

A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present technology may be assembler instructions, instruction-set-architecture (ISA) instructions, machine instructions, machine dependent instructions, microcode, firmware instructions, state-setting data, or either source code or object code written in any combination of one or more programming languages, including an object oriented programming language or a conventional procedural programming language. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to implement aspects of the present technology.

Aspects of the present technology have been described above with reference to flowchart illustrations and/or block diagrams of methods, apparatus (systems) and computer program products according to various embodiments. In this regard, the flowchart and block diagrams in the Figures illustrate the architecture, functionality, and operation of possible implementations of systems, methods and computer program products according to various embodiments of the present technology. For instance, each block in the flowchart or block diagrams may represent a module, segment, or portion of instructions, which comprises one or more executable instructions for implementing the specified logical function(s). It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Some specific examples of the foregoing may have been noted above but any such noted examples are not necessarily the only such examples. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It also will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 14:
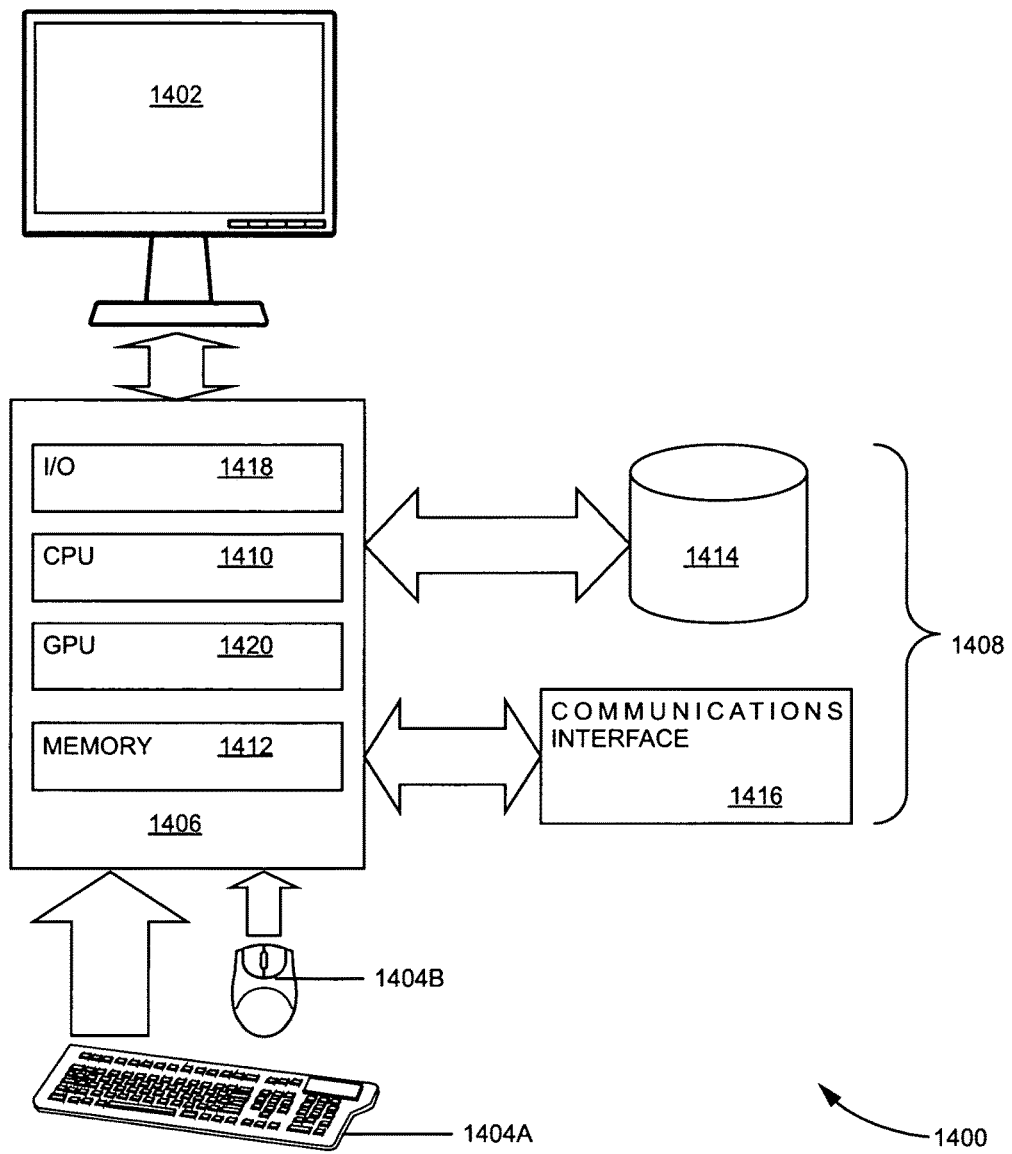
FIG. 14 is a block diagram of an exemplary computer system which may be used to implement aspects of the present disclosure.

An illustrative computer system in respect of which the technology herein described may be implemented is presented as a block diagram in FIG. 14. The illustrative computer system is denoted generally by reference numeral 1400 and includes a display 1402, input devices in the form of keyboard 1404A and pointing device 1404B, computer 1406 and external devices 1408. While pointing device 1404B is depicted as a mouse, it will be appreciated that other types of pointing device may also be used.

The computer 1406 may contain one or more processors or microprocessors, such as a central processing unit (CPU) 1410. The CPU 1410 performs arithmetic calculations and control functions to execute software stored in an internal memory 1412, preferably random access memory (RAM) and/or read only memory (ROM), and possibly additional memory 1414. The additional memory 1414 may include, for example, mass memory storage, hard disk drives, optical disk drives (including CD and DVD drives), magnetic disk drives, magnetic tape drives (including LTO, DLT, DAT and DCC), flash drives, program cartridges and cartridge interfaces such as those found in video game devices, removable memory chips such as EPROM or PROM, emerging storage media, such as holographic storage, or similar storage media as known in the art. This additional memory 1414 may be physically internal to the computer 1406, or external as shown in FIG. 14, or both.

The computer system 1400 may also include other similar means for allowing computer programs or other instructions to be loaded. Such means can include, for example, a communications interface 1416 which allows software and data to be transferred between the computer system 1400 and external systems and networks. Examples of communications interface 1416 can include a modem, a network interface such as an Ethernet card, a wireless communication interface, or a serial or parallel communications port. Software and data transferred via communications interface 1416 are in the form of signals which can be electronic, acoustic, electromagnetic, optical or other signals capable of being received by communications interface 1416. Multiple interfaces, of course, can be provided on a single computer system 1400.

Input and output to and from the computer 1406 is administered by the input/output (I/O) interface 1418. This I/O interface 1418 administers control of the display 1402, keyboard 1404A, external devices 1408 and other such components of the computer system 1400. The computer 1406 also includes a graphical processing unit (GPU) 1420.

The latter may also be used for computational purposes as an adjunct to, or instead of, the (CPU) 1410, for mathematical calculations.

The various components of the computer system 1400 are coupled to one another either directly or by coupling to suitable buses.

Thus, computer readable program code for implementing aspects of the technology described herein may be contained or stored in the memory 1412 of the computer 1406, or on a computer usable or computer readable medium external to the computer 1406, or on any combination thereof.

The term "computer system" and related terms, as used herein, is not limited to any particular type of computer system and encompasses servers, desktop computers, laptop computers, networked mobile wireless telecommunication computing devices such as smartphones, tablet computers, programmable logic controllers, as well as other types of computer systems.

Finally, the terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description has been presented for purposes of illustration and description, but is not intended to be exhaustive or limited to the form disclosed. Many modifications and variations will be apparent to those of ordinary skill in the art without departing from the scope of the claims. The embodiment was chosen and described in order to best explain the principles of the technology and the practical application, and to enable others of ordinary skill in the art to understand the technology for various embodiments with various modifications as are suited to the particular use contemplated.

The following references have been cited in the present document (this list is included for convenience, and none of the references is admitted to be prior art):

Amand L., Olsson G., and Carlsson B. (2013). Aeration control—a review. *Wat. Sci. & Tech.,* 67(11), 2374-2398.

Brewer, H. M., Stephenson, J. P. and Green, D. (1995). Plant Optimization Using Online Phosphorus Analyzers and Automated SRT Control to Achieve Harbour Delisting, *Proceedings of WEFTEC* 1995, Miami, Fla.

Ciancone, R., and T. Marlin (1992). Tune Controllers to Meet Plant Objectives. *Control,* 5, 50-57 (1992).

Dold, P. L., (2007). Quantifying Sludge Production in Municipal Treatment Plants. *Proceedings of WEFTEC* 2007, Oct. 13-17, San Diego, Calif.

Ekama, G. A., Wentzel, M. C. (2008). Chapters 4 and 5 in Biological Wastewater Treatment: Principles, Modelling and Design. IWA Publishing, London, UK.

Ekster, A. (2001). Automatic Waste Control. Proceedings of the 1st IWA International Conference on Instrumentation, Control and Automation (ICA), June 3-7, Malmö, Sweden.

Garrett, M. T. (1958). Hydraulic Control of Activated Sludge Growth Rate, *Sew. Ind. Wastes,* 39(3).

Langergraber, G., Alex, J., Weissenbacher, N., Woerner, D., Ahnert, M., Frehmann, T., Halft, N., Hobus, I., Plattes, M., Spering, V., Winkler, S. (2008). Generation of diurnal variation for dynamic simulation. *Wat. Sci. & Tech,* 59(9), 1483-1486.

Langergraber, G., Spering, V., Alex, J., Ahnert, M., Cernochoca, L., Dürrenmatt, D. J., Frehmann, T., Hobus, I., Weissenbacher, N., Winkler, S., Yücesoy, E. (2009). Using numerical simulation to optimize control strategies during activated sludge plant design. *Proceedings of the 10th IWA Conference on Instrumentation, Control and Automation (ICA),* June 14-17, Cairns, Australia.

Otterpohl, R. and Freund, M. (1992). Dynamic models for clarifiers of activated sludge plants with dry and wet weather flows. *Wat. Sci. & Tech,* 26(5-6), 1391-1400.

Rieger L., Takács I. and Siegrist H. (2012). Improving nutrient removal while reducing energy use at three Swiss WWTPs using advanced control. *Water Environ Res.,* 84(2), 171-189.

Rieger L., Jones R. M., Dold P. L. and Bott C. B. (2014). Ammonia-based feedforward and feedback aeration control in activated sludge processes. *Wat. Environ. Res.,* 86(1), 63-73.

Schraa O., Rieger L. and Alex J. (2016a). Coupling SRT control with aeration control strategies. *Proceedings of WEFTEC.* 16, New Orleans, La., USA.

Schraa O., Rieger L., and Alex J. (2016b). Development of a model for activated sludge aeration systems: linking air supply, distribution, and demand. *Wat. Sci. & Tech.,* published on-line October 2016.

Stephenson, J. P., Monaghan, B. A., and Laughton, P. J. (1981). Automatic Control of Solids Retention Time and Dissolved Oxygen in the Activated Sludge Process. *Wat. Sci. & Tech,* 13, pp. 751-758.

Takács, I. (2008). *Experiments in Activated Sludge Modelling.* PhD Thesis, Ghent University, Belgium, pp. 267.

Takács, I., Patry, G. G. and Nolasco, D. (1991). A dynamic model of the thickening/clarification process. *Wat. Res.,* 25(10), 1263-1271.

Takács I. and Patry G. G. (2002). The dynamic solids residence time. *Proceedings of IWA World Water Congress* 2002, Melbourne, Australia.

U.S. Environmental Protection Agency (USEPA), Office of Research and Development. (1989). Design Manual: Fine Pore Aeration Systems. EPA/625/1-89/023, U.S. E.P.A., Cincinnati, Ohio Vaccari, D. A., Cooper, A, Christodoulatos, C. (1988). Feedback control of activated sludge waste rate, *Journal WPCF,* 60, 1979-1985.

Vaccari D. A., Fagedes T. and Longtin J. (1985). Calculation of mean cell residence time for unsteady-state activated sludge systems. *Biotech. and Bioeng.,* 27, 695-703.

van Haandel, A. C., and van der Lubbe, J. G. M. (2012). Handbook of Biological Wastewater Treatment: Design and Optimisation of Activated Sludge Systems. IWA Publishing, London.

WEF (1997). *Automated Process Control Strategies.* Water Environment Federation, Alexandria, Va., USA.

One or more currently preferred embodiments have been described by way of example. It will be apparent to persons skilled in the art that a number of variations and modifications can be made without departing from the scope of the claims. In construing the claims, it is to be understood that the use of a computer to implement the embodiments described herein is essential.

What is claimed is:

1. A method of supervisory control for an activated sludge-based water resource recovery facility, the method comprising:

for at least one aeration tank:
measuring total ammonia nitrogen in a volume of sludge in the at least one aeration tank;
comparing the measured total ammonia nitrogen to a target ammonia nitrogen setpoint to calculate a target dissolved oxygen setpoint for adjusting the measured total ammonia nitrogen toward the target ammonia nitrogen setpoint;
measuring dissolved oxygen in the volume of sludge in the at least one aeration tank;
comparing the measured dissolved oxygen to the target dissolved oxygen setpoint to calculate a target airflow setpoint for adjusting the measured dissolved oxygen toward the target dissolved oxygen setpoint;
adjusting airflow into the at least one aeration tank toward the target airflow setpoint;
comparing the target dissolved oxygen setpoint to a desired dissolved oxygen concentration to calculate a target solids retention time setpoint, wherein the desired dissolved oxygen concentration is a filtered or averaged version of the target dissolved oxygen setpoint; and
adjusting a solids retention time for the at least one aeration tank toward the target solids retention time setpoint;
wherein adjusting the solids retention time for the at least one aeration tank toward the target solids retention time setpoint comprises adjusting a waste activated sludge flow rate.

2. The method of claim 1, wherein:
adjusting the waste activated sludge flow rate comprises:
comparing the target solids retention time setpoint to a calculated dynamic solids retention time to calculate a target mixed liquor suspended solids setpoint;
measuring mixed liquor suspended solids concentration in the at least one aeration tank;
comparing the measured mixed liquor suspended solids concentration to the target mixed liquor suspended solids setpoint to calculate a target waste activated sludge flow rate setpoint; and
adjusting the waste activated sludge flow rate toward the target waste activated sludge flow rate setpoint.

3. The method of claim 2, wherein the calculated dynamic solids retention time is obtained by:

$$dSRT/dt = 1 - SRT(F\_p)/M$$

where:
dSRT/dt=age change of solids (change in age of solids [in days] per days of real time);
M=mass of solids in the system;
F_p=mass flow of solids produced in the system;
and where:

$$F\_p = (M - M\_o)/\Delta t + Q\_w X\_w + Q\_e X\_e$$

where:
M=mass of total or volatile solids in the system at the current time (g);
M_o=mass of total or volatile solids in the system at the previous time interval (g);
Δt=time interval between calculations of the sludge production (d);
Q_w=waste flow rate (m³/d);
X_w=total or volatile solids concentration of waste stream (g/m³);
Q_e=secondary effluent flow rate (m3/d); and
X_e=total or volatile solids concentration of secondary effluent stream (g/m3).

4. The method of claim 2, wherein the calculated dynamic solids retention time is obtained by:

$$SRT = \frac{X_{MLSS} V_a}{X_{RAS} Q_w + X_e Q_e}$$

where:
$V_a$=total volume of aeration tanks, m³;
$X_{MLSS}$=total or volatile suspended solids concentration in the mixed liquor, mg/L;
$X_{RAS}$=total or volatile suspended solids concentration in the return activated sludge (RAS), mg/L;
$X_e$=total or volatile suspended solids concentration in the secondary effluent, mg/L;
$Q_w$=waste activated sludge flow rate, m³/d; and
$Q_e$=secondary effluent flow rate, m³/d.

5. The method of claim 4, further comprising applying a low-pass filter to the calculated dynamic solids retention time or to measured quantities used in its calculation.

6. The method of claim 5, wherein adjusting airflow into the aeration tank toward the target airflow setpoint comprises the dissolved oxygen controller adjusting airflow directly by controlling at least one valve.

7. The method of claim 5, wherein adjusting airflow into the aeration tank toward the target airflow setpoint comprises the dissolved oxygen controller adjusting airflow indirectly by sending the target airflow setpoint to an airflow controller that controls the valve, wherein the airflow controller receives feedback from a measured airflow.

8. The method of claim 2, wherein:
the target average dissolved oxygen setpoint is calculated by an ammonia controller;
the target airflow setpoint is calculated by a dissolved oxygen controller;
the target solids retention time setpoint is calculated by a supervisory controller;
the target mixed liquor suspended solids setpoint is calculated by a solids retention time controller; and
the target waste activated sludge flow rate setpoint is calculated by a mixed liquor suspended solids controller.

9. The method of claim 8, wherein each of the ammonia controller, the dissolved oxygen controller, the supervisory controller, the solids retention time controller and the mixed liquor suspended solids controller are distinct individual programmable logic controllers.

10. The method of claim 8, wherein each of the ammonia controller, the dissolved oxygen controller, the supervisory controller, the solids retention time controller and the mixed liquor suspended solids controller are software modules executing in at least one processor of a computer.

11. The method of claim 1, wherein:
the target dissolved oxygen setpoint is calculated by an ammonia controller;
the target airflow setpoint is calculated by a dissolved oxygen controller; and
the target solids retention time setpoint is calculated by a supervisory controller.

12. The method of claim 1, wherein:
the at least one aeration tank comprises a plurality of aeration tanks; and
adjusting the solids retention time for the at least one aeration tank toward the target solids retention time setpoint comprises temporarily ceasing inflow to at least one of the plurality of aeration tanks.

13. The method of claim 1, wherein:
the airflow is intermittent; and
adjusting airflow into the at least one aeration tank toward the target airflow setpoint comprises adjusting aeration period length.

14. The method of claim 1, further comprising adding nitrifying sludge to the at least one aeration tank;
wherein adjusting a solids retention time for the at least one aeration tank toward the target solids retention time setpoint accounts for addition of the nitrifying sludge.

15. The method of claim 1, wherein:
support media are disposed within the at least one aeration tank;
the support media being adapted to allow biofilm growth on the support media.

16. The method of claim 1, wherein the at least one aeration tank comprises at least one granular sludge reactor.

17. A method of supervisory control for an activated sludge-based water resource recovery facility, comprising for at least one sequencing batch reactor (SBR) in the water resource recovery facility:
measuring total ammonia nitrogen in a volume of sludge in the at least one SBR during an aerobic phase of the at least one SBR;
comparing the measured total ammonia nitrogen to a target ammonia nitrogen setpoint to calculate a target aerobic phase length;
adjusting a duration of airflow into the at least one SBR toward the target aerobic phase length;
comparing the target aerobic phase length to an average aerated phase length to calculate a target solids retention time setpoint; and
adjusting a waste activated sludge flow rate for the at least one SBR during the aerobic phase according to the target solids retention time setpoint.

18. The method of claim 17, wherein the at least one SBR comprises at least one granular sludge reactor.

* * * * *

UNITED STATES PATENT AND TRADEMARK OFFICE
CERTIFICATE OF CORRECTION

PATENT NO. : 10,399,876 B2
APPLICATION NO. : 15/712601
DATED : September 3, 2019
INVENTOR(S) : Schraa et al.

It is certified that error appears in the above-identified patent and that said Letters Patent is hereby corrected as shown below:

In the Claims

In Claim 3:
Column 24, Line 4, "(m3/d)" should read: --($m^3/d$)--; and
Column 24, Line 6, "(g/m3)." should read: --($g/m^3$).--.

Signed and Sealed this
Thirty-first Day of December, 2019

Andrei Iancu
*Director of the United States Patent and Trademark Office*